US010720029B1

(12) United States Patent
Mears

(10) Patent No.: US 10,720,029 B1
(45) Date of Patent: Jul. 21, 2020

(54) MEDICAL DEVICE ALERT, OPTIMIZATION, PERSONALIZATION, AND ESCALATION

(71) Applicant: Roche Diabetes Care, Inc., Indianapolis, IN (US)

(72) Inventor: Mark Gilmore Mears, Indianapolis, IN (US)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 0 days.

(21) Appl. No.: 16/268,453

(22) Filed: Feb. 5, 2019

(51) Int. Cl.
*A61B 5/00* (2006.01)
*G08B 3/10* (2006.01)
(Continued)

(52) U.S. Cl.
CPC .......... *G08B 3/1066* (2013.01); *A61B 5/1176* (2013.01); *A61B 5/121* (2013.01); *A61B 5/74* (2013.01); *A61B 5/7405* (2013.01); *A61B 5/746* (2013.01); *A61B 5/7455* (2013.01); *G16H 10/60* (2018.01); *G16H 40/63* (2018.01); *G16H 50/30* (2018.01); *H03G 3/32* (2013.01); *H04L 67/18* (2013.01); *H04L 67/306* (2013.01); *A61B 5/14532* (2013.01); *A61B 2560/0242* (2013.01); *H04R 2430/01* (2013.01)

(58) Field of Classification Search
CPC ......... A61B 5/74; A61B 5/145; A61B 5/7405; A61B 5/746; A61B 5/7475; A61B 5/1112; H04M 1/72591
See application file for complete search history.

(56) References Cited

U.S. PATENT DOCUMENTS 8,487,758 B2 7/2013 Istoc et al.
8,594,738 B2 11/2013 Cook et al.
(Continued)

FOREIGN PATENT DOCUMENTS

EP 2256494 A1 12/2010
EP 3063686 A2 9/2016
WO WO 2011-060908 A2 5/2011

OTHER PUBLICATIONS

Amy Judd. "LISTEN: New backup technology developed to replace 'beep beep' sound", Available at https://globalnews.ca/news/1814857/listen-new-backup-technology-developed-to-replace-beep-beep-sound/ Feb. 5, 2015, Retrieved Oct. 29, 2018, 2 pages.
(Continued)

*Primary Examiner* — Benyam Haile
(74) *Attorney, Agent, or Firm* — Flaster Greenberg P.C.

(57) ABSTRACT

An alert is used to inform a user that their blood glucose level has dropped below a threshold (e.g., the user is hypoglycemic) or has increased above a threshold (e.g., the user is hyperglycemic). There is a hierarchy of alerts from lowest priority to highest priority. The alert is communicated by a user device (e.g., a mobile device), which is, for example, a smartphone, smart watch, home automation device, or the like. The alert is modified in order to increase the likelihood that the user receives or acknowledges the alert within a minimal amount of time. An intensity level (e.g., a volume) of an alert is modified based on, for example, whether the user has acknowledged a previous alert. A modality or a sensory channel of an alert is changed if an initial alert does fails to elicit a response from the user.

32 Claims, 13 Drawing Sheets

(51) Int. Cl.
*H04L 29/08* (2006.01)
*A61B 5/1171* (2016.01)
*A61B 5/12* (2006.01)
*G16H 10/60* (2018.01)
*G16H 50/30* (2018.01)
*G16H 40/63* (2018.01)
*H03G 3/32* (2006.01)
*A61B 5/145* (2006.01)

(56) References Cited

U.S. PATENT DOCUMENTS

| | | | |
|---|---|---|---|
| 8,773,257 B2 | 7/2014 | Yodfat et al. | |
| 9,084,080 B2 | 7/2015 | Cook et al. | |
| 9,344,815 B2 | 5/2016 | Selig et al. | |
| 9,380,982 B2 | 7/2016 | Battista et al. | |
| 9,415,157 B2 | 8/2016 | Mann et al. | |
| 9,654,956 B2 | 5/2017 | Lim et al. | |
| 9,847,038 B2 | 12/2017 | Mayou et al. | |
| 9,929,709 B1 | 3/2018 | Yang et al. | |
| 9,974,903 B1 | 5/2018 | Davis et al. | |
| 2004/0243677 A1* | 12/2004 | Curbow | G06Q 10/107 709/206 |
| 2005/0016532 A1 | 1/2005 | Farrell et al. | |
| 2008/0122582 A1 | 5/2008 | Baker et al. | |
| 2008/0300572 A1* | 12/2008 | Rankers | A61B 5/14532 604/504 |
| 2009/0240128 A1 | 9/2009 | Mensinger et al. | |
| 2010/0268051 A1* | 10/2010 | Prasad | A61B 5/0002 600/365 |
| 2011/0050428 A1 | 3/2011 | Istoc et al. | |
| 2013/0091229 A1* | 4/2013 | Dunn | G06Q 50/01 709/206 |
| 2016/0044151 A1 | 2/2016 | Shoemaker et al. | |
| 2016/0205267 A1* | 7/2016 | Vaughn | H04M 19/04 455/566 |
| 2017/0181645 A1* | 6/2017 | Mahalingam | A61B 5/0205 |
| 2017/0330439 A1 | 11/2017 | Zhou et al. | |

OTHER PUBLICATIONS

Federal Signal "253 Vehicular Back-up Alarm", Available at https://www.fedsig.com/product/253-vehicular-back-up-alarm%20%20%20%20%20#product-block-l Retrieved Oct. 29, 2018, 4 pages.
Lovejoy, "Patent application shows how Apple Watch could measure ambient sound to adjust volume of iPhone alerts", Available at https://9to5mac.com/?s=patent+application+shows+how+apple+watch+could+measure+ambient+sound+to+adjust+volume+of+iphone+alerts Feb. 11, 2016, Retrieved Oct. 29, 2018, 2 pages.
Balazsorban44, "google-calednar-web-material", Available at https://github.com/balazsorban44/google-calendar-web-material Retrieved Oct. 29, 2018, 2 pages.

* cited by examiner

MEDICAL DEVICE ALERT, OPTIMIZATION, PERSONALIZATION, AND ESCALATION

BACKGROUND

Devices are used to alert a user during a potential medical emergency. The user may be a person with diabetes (user), and the alert is a diabetes-related alert. For example, the user's device may alert the user that the user's blood sugar is below a threshold (e.g., the user is hypoglycemic) or above a threshold (e.g., the user is hyperglycemic).

The alert volume at which these devices deliver alerts may be at a suboptimal level given the environment of the user. The alert volume may be too soft given the environment. For example, the user may be in a relatively loud environment (e.g., a sporting event) where the user may not hear an alert that would otherwise be audible. Alternatively, the alert volume may be too loud given the environment. For example, the user may be in an environment where loud noise is discouraged (e.g., a movie theater, church, library, or another location at which loud noises are discouraged). The user may decrease the volume of the alert or disable the alert entirely, which may lead to the user missing further alerts.

A user may fail to receive or react to these alerts, for example because the alert volume is too low to be heard, the user is away from the mobile device, or the user is asleep. The user's failure to receive or react to an alert may lead to negative consequences for the user. For example, the user may become hypoglycemic or hyperglycemic. The user's unresponsiveness to a given alert also causes unnecessary processing of alerts at the user's device, which results in unnecessary depletion of battery power for battery-powered devices and may eventually result in total battery depletion, which leads to an inability of the device to alert the user of further events.

The user's blood glucose level is monitored by a blood glucose monitor (BGM) or a continuous glucose meter (CGM) that is implanted into or otherwise physically connected to the user. Defects may arise in these glucose monitoring devices. For example, the sensor may be out of calibration, too hot or too cold, or otherwise unable to perform its functions. When alerts from the user's devices are poorly communicated, the user fails to receive alerts indicating the defects with the glucose monitoring devices, which may cause the user to be unaware of alerts and subsequently become hypoglycemic or hyperglycemic.

SUMMARY

A user device is implemented to provide diabetes-related alerts to a user. The alerts are used to inform a user that their blood glucose level has dropped below a threshold (e.g., the user is hypoglycemic) or has increased above a threshold (e.g., the user is hyperglycemic). The alerts are used to inform the user of a problem with a device for monitoring or treating a diabetic condition.

The alert is modified in order to increase the probability that the user receives and acknowledges the alert within a minimal amount of time. There are multiple types of alerts (e.g., real-time alerts, predictive alerts, or another type of alert). For example, the alert is customized to the user and to the user's environment. In addition, the alert is modified in order to reduce the power used by a user device to send the alert. Reducing the power used by the user device to send the alert allows the user device to remain powered for a longer time. The alerts include notifications to the user of technical issues with the user device or connected devices (e.g., a glucose monitoring device implanted in the user).

An intensity level (e.g., a volume) of an alert is modified based on, for example, whether the user has acknowledged a previous alert. For example, an alert is initially presented at a low priority. If the user does not acknowledge the alert within a given time period, the alert is repeated until the user acknowledges the alert. The intensity of the alert is increased by a just-noticeable difference (JND) each time the alert is repeated. The user device records the intensity level at which the user acknowledged the alert and adjusts the level of future alerts based on the recorded level.

The user device adjusts the baseline intensity level of the initial alert or the repeated alerts based on a user-specific criteria. The user-specific criteria is an age of the user, a gender of the user, a physical condition of the user, a mental condition of the user, or the like. For example, the user may have age-related hearing loss, and the volume of an auditory alert is increased to offset the hearing loss. The volume of any further alerts is further increased by a just-noticeable difference. If the alert is a visual alert (e.g., flashing lights or a visual notification on the user device), the baseline intensity level of the initial alert is increased if, for example, the user has a condition that impairs their vision.

A sensory channel of an alert is changed if an initial alert fails to elicit a response from the user. An initial alert is presented in a given sensory channel (e.g., a visual alert, a haptic alert, an auditory alert, or the like). If the user does not acknowledge the initial alert, a further alert is presented in a second sensory channel. For example, an initial alert is presented as a haptic signal to the user. For example, the user device vibrates for the initial alert. If the user fails to acknowledge the haptic signal, a second alert is presented as an auditory signal to the user. The auditory signal is a tone associated with a specific medical condition. Alternatively, the user device calls, texts, or otherwise attempts to contact the user or an emergency contact. The user device notifies emergency services that the user has a medical emergency and sends the location of the user device to the emergency services.

Different types of alerts within a single sensory channel are used. For example, an initial auditory alert is relatively simple (e.g., a beep, a ringtone, a notification sound, or any combination thereof. If the user does not acknowledge the initial auditory alert, the user device delivers a second auditory alert that has a higher priority level and is more intense. The second auditory alert is, for example, a short-spoken phrase, a piece of music, or the like.

The user device sets an upper limit on an intensity level of an alert. For example, the user device sets a maximum volume for an auditory alert or a brightness maximum for a visual alert. The maximum intensity level is determined based on the priority level of the alert. For example, a higher priority alert (e.g., that the user is currently hyper- or hypoglycemic) has a higher intensity level than a lower priority alert (e.g., a daily reminder). If an alert reaches the maximum intensity level, the user device delivers any further alerts at the maximum intensity level.

The user device limits the modalities that an alert uses based on priority level of the alert. For example, the higher priority alert is presented using auditory, visual, and haptic signals, and a lower priority alert is presented using auditory signals. The user device delivers an alert in a specific sequence of modalities, multiple modalities at once, or a sequence of multiple modalities. For example, the initial alert is presented as an auditory signal, a second alert is presented as an auditory signal and a haptic signal, and a third alert is presented as an auditory signal, a haptic signal, and a visual signal.

An intensity level of an alert is modified based on an environment in which the user is located. For example, the alert is an auditory alert. The user may be in an environment where the ambient noise level is above average (e.g., a sporting event, party, restaurant, or the like). The volume of the alert is increased in order to be audible to the user above the ambient noise. If the user does not acknowledge the alert, the volume of repeated alerts is further increased by a JND until the user acknowledges the alert. Alternatively, the user may be in an environment where the ambient noise level is below average (e.g., a library, the user's home, or the like) or where loud noises are discouraged (e.g., a religious service, wedding, movie theater, or the user's workplace). The volume of the alert is decreased in order to avoid startling or embarrassing the user. If the user does not acknowledge the alert, the volume of repeated alerts is increased above the minimum volume. There is a volume threshold that an alert may not exceed. The intensity level of a non-auditory alert (e.g., a visual alert) is similarly changed based on the environment.

In order to determine an acceptable intensity level, the user device samples a relevant characteristic of the environment. For example, for an auditory alert, the user device uses an internal or connected microphone to sample the ambient noise level of the environment. For a visual alert, the user device uses an internal or connected camera to sample the ambient brightness of the environment. The user device uses information from the user's calendar or schedule to determine the appropriate intensity level. For example, the user device has access to an online calendar detailing the user's schedule. If the calendar contains an entry at the time of the alert, the user device uses information from the entry (e.g., the entry title, location, type, or the like) to determine the appropriate intensity level.

The user device has access to information regarding the location of the user or the user device, and uses the information regarding the location to determine the appropriate intensity level. For example, the user device has access to GPS data, WIFI data, or other data that indicates the location of the user device or the user. The user device uses the location information to determine a general categorization for the location and adjusts the intensity level of the alert correspondingly. For example, the user device uses GPS data to determine that the user device is located in or near a church, and decreases the intensity level of the alert.

The user device is connected to one or more other devices that are used to alert the user if the user fails to acknowledge an alert from the user device (e.g., if the user is away from the user device). For example, the user device is connected to the other device via a wireless connection (e.g., WIFI, Bluetooth, LTE, or the like). The other device is any IoT device (e.g., a smartwatch, a home automation device, or the like). The other device may be in approximately the same location as the user device, or the other device may be located remotely from the user device.

The user device sends a notification to the other device to deliver an alert to the user if the user does not acknowledge an alert from the user device. For example, the user device is a smartphone, and sends a notification to a smartwatch worn by the user to deliver an alert to the user. The alert presented by the other device is any type of alert as described herein. The user device uses information about the location of the other devices or the user to determine which other device to send the notification to.

In an example embodiment, a first non-audible alert is provided using at least a first sensory channel on a mobile device associated with a user in response to detection of a triggering event for communicating a diabetes-related alert to the user. The first non-audible alert comprises an alert message on a display of the mobile device and a vibration of the mobile device.

A second non-audible alert is provided using the at least the first sensory channel on the mobile device associated with the user. The second non-audible alert has a higher priority level than the first non-audible alert. The second non-audible alert is provided in response to an indication of user acknowledgement of the first non-audible alert failing to be received after the first non-audible alert has been provided a predefined number of times. The second non-audible alert comprises the alert message on the display of the mobile device, a vibration of the mobile device, and a flashing LED on the mobile device.

A first audible alert is provided using a second sensory channel on the mobile device associated with the user. The first audible alert has a higher priority level than the second non-audible alert. The first audible alert is provided in response to an indication of user acknowledgement of the second non-audible alert failing to be received after the second non-audible alert has been provided a predefined number of times. The first audible alert comprises the alert message on the display of the mobile device and an audible version of the alert message read at a first volume level via a speaker of the mobile device using a text-to-speech service.

A second audible alert is provided using the second sensory channel on the mobile device associated with the user. The second audible alert has a higher priority level than the first audible alert. The second audible alert is provided in response to an indication of user acknowledgement of the first audible alert failing to be received after the first audible alert has been provided a predefined number of times. The second audible alert comprises the alert message on the display of the mobile device and an auditory alert notification at a first volume level via a speaker of the mobile device.

In an example embodiment, the first audible alert is provided at a second volume level louder than the first volume level of the first audible alert. The first audible alert is provided at the second volume level in response to the indication of user acknowledgement of the first audible alert failing to be received after the first audible alert has been provided and before the first audible alert has been provided the predefined number of times.

In an example embodiment, the second audible alert is provided at a second volume level louder than the first volume level of the second audible alert. The second audible alert is provided at the second volume level in response to the indication of user acknowledgement of the second audible alert failing to be received after the second audible alert has been provided and before the second audible alert has been provided the predefined number of times.

In an example embodiment, an external alert is provided from the mobile device to an external source in response to the indication of user acknowledgement of the second audible alert failing to be received after the second audible alert has been provided the predefined number of times. In an example, the external source is a home automation system.

In an example embodiment, a diabetes-related alert is communicated to a user via an audible alert on a mobile device associated with the user. The audible alert is communicated in response to detection of a triggering event for communicating the diabetes-related alert to the user. A volume level of the audible alert is increased until a maximum volume level is reached in response to an indication of user acknowledgement of the audible alert failing to be received after a predetermined period of time. One or more diabetes-related alerts is generated in an order of a predefined hierarchy of alerts. The diabetes-related alerts are generated in response to the indication of user acknowledgement of the audible alert failing to be received and after the maximum volume level is reached. The predefined hierarchy of alerts comprises two or more of: a predefined speech for the one or more diabetes-related alerts that is configured to be sent to a speaker device for audible communication to an occupant of a space; a predefined message for the one or more diabetes-related alerts that is configured to be sent via telecommunication or text message using an alternate device to the mobile device; a predefined message for the one or more diabetes-related alerts that is configured to be sent via an instant messaging service; or a message for the one or more diabetes-related alerts that is configured to be sent to provide an alert via a home automation system. In an example, the predefined speech includes a name of the user. A last known location of the mobile device is communicated to at least one emergency contact or emergency service in response to an indication of user acknowledgement of the predefined hierarchy of alerts failing to be received after a predefined period of time.

In an example embodiment, a lack of movement of the user is sensed via the mobile device over a period of time after the detection of the triggering event. A determination is made that the lack of movement matches a sleep state or a hypoglycemic state. An emergency service is contacted in response to the lack of movement matching the hypoglycemic state.

In an example embodiment, the home automation system comprises a diabetes notification lamp. The message is configured to control the diabetes notification lamp to provide the one or more diabetes-related alerts.

DETAILED DESCRIPTION

Figure 1:
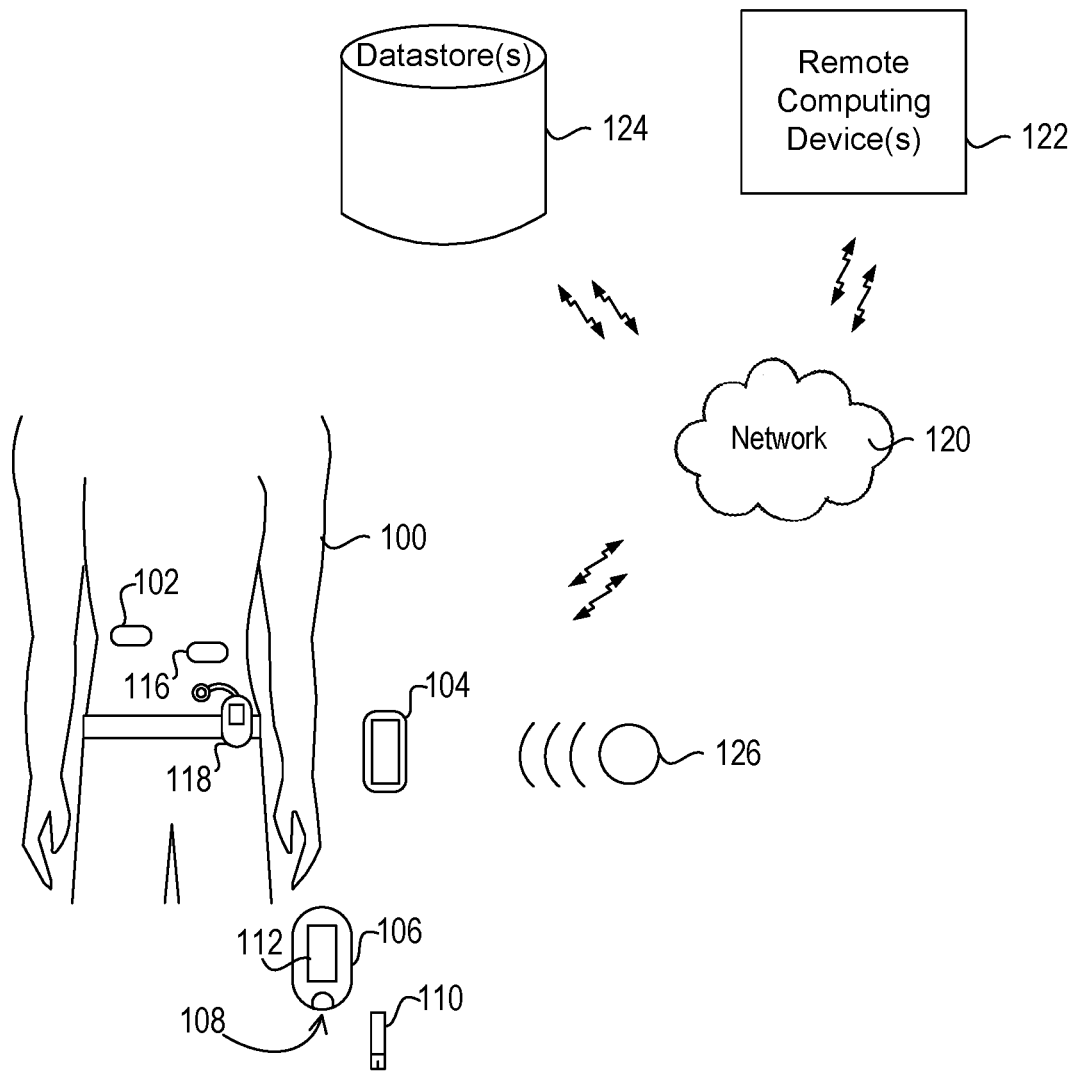
FIG. 1 is a perspective view of a representative environment for monitoring or treating a diabetic condition.

FIG. 1 is a perspective view of a representative environment for monitoring or treating a diabetic condition. As shown in FIG. 1, a user 100 with diabetes uses one or more blood glucose monitoring devices to help monitor or treat the diabetic condition. The diabetic condition includes a metabolic syndrome, pre-diabetes, type 1 diabetes, type 2 diabetes, or gestational diabetes. The user 100 may be in an extreme diabetic state, such as hypoglycemia or hyperglycemia, when the blood glucose level of the user 100 is above or below a threshold blood glucose level. In the embodiment of FIG. 1, the user 100 uses a blood glucose monitoring device to monitor blood glucose levels.

As used herein, the term "blood glucose monitoring device" refers to any device that detects and reports a level of glucose in the blood of the user, either through direct measurement of the blood or through an indirect detection process. A blood glucose level is also referred to as a blood sugar level. Examples of blood glucose monitoring devices include, but are not strictly limited to, continuous glucose monitoring devices, flash glucose monitoring devices, and blood glucose meters that provide a single measurement of blood glucose levels from a blood sample in a "spot" monitoring process. FIG. 1 depicts examples of blood glucose monitoring devices that are described in more detail below.

In some embodiments, the blood glucose monitoring device is a continuous glucose monitor (CGM) 102. The CGM 102 includes a subcutaneous sensor that is used to sense and monitor the amount of glucose in interstitial fluid of the user 100. The CGM 102 includes a transmitting device that is located directly over the sensor that wirelessly powers the data transfer from the sensor. The CGM 102 periodically communicates data indicating the blood glucose levels of the user 100 to an external device, such as a mobile device 104, for computing or storing the blood glucose levels of the user 100.

As used herein, the term "mobile device" refers to any mobile electronic device that is capable of moving with a user as the user changes locations. Example mobile devices include mobile phones, smartphones, wearable devices, tablets, laptops, notebook computers, personal digital assistants (PDAs), and any other mobile electronic device that is capable of moving with a user. Some embodiments of the mobile device incorporate the blood glucose monitor into an integrated device.

Some embodiments of the mobile device 104 operate as a CGM controller device. Though the mobile device 104 is provided as an example of a device with which the CGM 102 communicates, the CGM 102 may communicate with other dedicated CGM controller devices for providing similar functionality that is described herein for the mobile device 104. The CGM 102 processes the blood glucose data for providing alerts, or the blood glucose data is processed at the mobile device 104, or other CMG controller device, an alert indicator is communicated to the CGM 102.

In some embodiments, the blood glucose monitoring is performed by flash glucose monitoring (FGM). The FGM includes a subcutaneous sensor 103 that is used to sense and monitor the amount of glucose in interstitial fluid of the user 100. A separate reader device, such as the mobile device 102 or another reader device, receives the blood glucose information from the sensor when the device is within the RF range of the sensor 103. The sensor 103 transmits an instantaneous blood glucose level or a graphical trend of the blood glucose level to the reader device for display.

The user 100 uses a blood glucose meter (BGM) 106 as a blood glucose monitoring device to monitor blood glucose levels. The BGM 106 includes port 108 that receives a blood glucose measurement strip 110. The user 100 deposits a sample of blood on the blood glucose measurement strip 110. The BGM 106 analyzes the sample and measure the blood glucose level in the sample. The blood glucose level measured from the sample is displayed on a display 112 of the BGM 106 or communicated to an external device, such as the mobile device 104.

The blood glucose level measured by the BGM 106 or computed using data received from the CGM 102 is used to treat the diabetic condition of the user 100. For example, the user 100 uses an ambulatory non-durable insulin pump 116 or an ambulatory durable insulin pump 118 to treat the diabetic condition with insulin. The mobile device 104 determines an amount of insulin to be administered to the user 100 and the insulin pump 116, 118 receives instructions from the mobile device 104 to deliver a predetermined amount of insulin to the user 100. The insulin pump 116, 118 receives other information from the mobile device 104, such as mealtime information or exercise information of the user 100. The insulin pump 116, 118 determines the amount of insulin to administer based on the received information from the mobile device 104. The insulin pump 116, 118 communicates information to the mobile device 104. The information communicated to the mobile device 104 includes an amount of insulin delivered to the user 100, corresponding times of delivery, or a pump status (e.g., battery status, insulin status, or another status of a portion of the pump).

The mobile device 104 communicates with the insulin pump 116, 118, the CGM 102, or the BGM 106 using wired or wireless communications. The mobile device 104, the CGM 102, a CGM controller, the BGM 106, or the insulin pump 116, 118 are collectively referred to as user devices. The mobile device 104 communicates with the insulin pump 116, 118, the CGM 102, or the BGM 106 using the same or different wireless protocols. For example, the mobile device 104 communicates with the insulin pump 116, 118, the CGM 102, or the BGM 106 using BLUETOOTH®, near field communication (NFC), THREAD®, WIFI®, ZIGBEE®, WI-MAX®, a cellular communication protocol, a proprietary wireless communication protocol, or another radio frequency (RF) communication protocol.

The mobile device 104 receives data and stores data for assisting in monitoring or treating the diabetic condition. The mobile device 104 receives input from the user 104 via a user interface being provided on a display. The mobile device 104 receives input via hard buttons or soft buttons provided on the display.

The mobile device 104 is configured to determine the device's location. For example, the mobile device 104 is able to determine the geolocation (e.g., latitude and longitude) of the device using signals from a global positioning system (GPS) or triangulation via cellular communications. The mobile device 104 determines a relative location using an RF beacon device 126. The RF beacon device 126 communicates a unique identifier via a short-range wireless communication, such as a BLUETOOTH® low energy (BLE) beacon or an NFC beacon. The mobile device 104 receives the RF beacon and perform a lookup in a database (e.g., in information from the datastores 124) to determine a relative location associated with the unique identifier. For example, the mobile device 104 determines that the RF beacon indicates that the device is in a particular room in a home or building, on a certain floor in a building, close to a predefined object, or is within the RF range of a beacon associated with another object or location.

Some embodiments of the mobile device 104 include one or more sensors for detecting a relative position of the device or information about the user 100. The mobile device 104 detects a movement or a change in orientation. Based on the movement or change in orientation (or lack thereof) of the mobile device 104 over a period of time, the mobile device 104 detects that the user 100 is standing, sitting, or lying down. The mobile device 104 detects that the user 100 is exercising when the movement or a change in orientation is greater than a threshold for a period of time. The mobile device 104 detects the heartrate of the user 100 using a heartrate sensor. Based on the heartrate and the movement of the user 100 over a period of time, the mobile device 104 detects whether the user 100 is asleep or awake. The information about the mobile device 104 or the user 100 is used to provide information about or treat the diabetic condition.

The mobile device 104 provides information to the user 100 about the user's diabetic condition. For example, the mobile device 104 provides blood glucose levels, provides meal-related information, provides exercise-related information, generates graphs and other graphical user interfaces for display, or generates alerts that are provided to the user 100. For example, the mobile device 104 measures the blood glucose level of the user 100 and provide an alert when the blood glucose level of the user 100 has reached a threshold for an extreme diabetic state (e.g., hypoglycemia or hyperglycemia). The alerts provided by the mobile device 104 are audible or non-audible alerts. The non-audible alerts are provided as a vibration, a flashing of the screen, or a flashing of an LED on the mobile device 104. The alerts also, or alternatively, are provided by an external device based on a communication from the mobile device 104. Some embodiments of the mobile device 104 include an electric motor for providing on-body vibration alerts or a speaker for providing audible alerts in response to data indications or triggers identified in the monitored blood glucose data.

The mobile device 104 communicates with other devices directly via a wired communication or a short-range wireless communication (e.g., WI-FI®, BLUETOOTH®, BLE, NFC, or another suitable short-range wireless communication). The mobile device 104 communicates indirectly with remote computing devices 122 or datastores 124 via a network 120 (e.g., using a WI-FI® network, a cellular network, a WI-MAX® network, or another wired or wireless network). The network 120 is a wired or wireless network. The network 120 is used to communicate over the Internet to other devices.

The mobile device 104 communicates with the remote computing devices to generate user interfaces for display on the mobile device 104, perform remote computation, or to otherwise control a remote computing device. For example, the mobile device 104 provides a user interface via an application or web browser that is generated at a remote computing device 122. The mobile device 104 generates instructions for providing alerts via remote computing devices 122 based on information received from the user 100, the CGM 102, the BGM 106, or the insulin pump 116, 118. Example remote computing devices 122 to which the mobile device 104 sends communications for performing alerts include a remote computer (e.g., a server, a laptop, or other computer), an external speaker, an external display device (e.g., television, monitor, or another device having an external display), a home automation system, remote telecommunications devices (e.g., for sending text or voice communications to an emergency contact over a telecommunications network), or another remote computing device.

The mobile device 104 communicates with the datastores 124 to store information or retrieve information. The information includes information related to the user 100, the CGM 102, the BGM 106, or the insulin pump 116, 118. For example, the mobile device 104 receives treatment information associated with the user 100 as input or receive blood glucose information from the CGM 102 or the BGM 106 and send the information to the datastores 124 via the network 120. Stored information is retrieved from the datastore 124 for treatment of the diabetic condition of the user. For example, the mobile device 104 retrieves an amount of insulin delivered to the user 100 or corresponding times of delivery. The datastores 124 include one or more remote storage locations, which are collectively referred to as cloud storage. For example, the datastores 124 store information regarding one or more personal characteristics of the user 100 (e.g., the user's age or gender) or one or more alert profiles for an alert.

One or more of the user devices are implemented to provide diabetes-related alerts to a user. The alerts are used to inform a user that their blood glucose level has dropped below a threshold (e.g., the user is hypoglycemic) or has increased above a threshold (e.g., the user is hyperglycemic). The alerts are also used to inform the user of a problem with a device for monitoring or treating a diabetic condition. To better ensure that the user receives the alerts regarding the user's diabetic condition or the status of the user's devices for monitoring or treating the diabetic condition, an alert is modified based on user input, lack of user input, user-specific characteristics, or the user environment.

Figure 2:
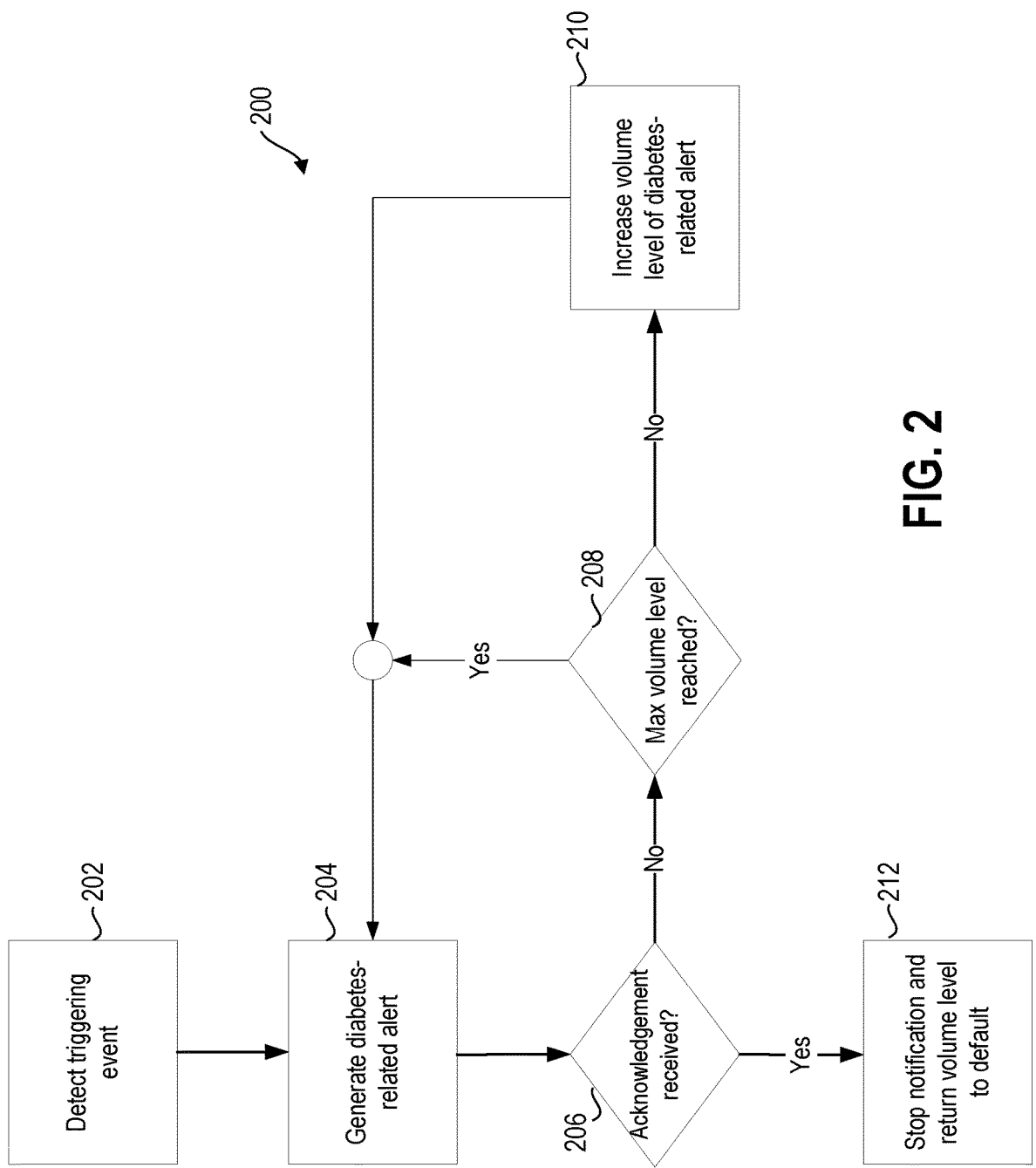
FIG. 2 shows a flowchart of an example process for increasing an alert volume when a diabetes-related alert is unacknowledged by a user.

FIG. 2 shows a flowchart of an example process 200 for increasing an alert volume when a diabetes-related alert is unacknowledged by a user. The example process 200 is performed by one or more devices, such as one or more user devices, for example. The process 200 is performed by a single user device, or distributed across multiple devices.

As illustrated in FIG. 2, a triggering event is detected at 202 for communicating a diabetes-related alert to a user. The triggering event is detected when a blood glucose level of the user is above a high-end threshold or below a low-end threshold. The alert is generated by a user device (e.g., a smartphone, wearable device, a CGM, a CGM controller, a BGM, an insulin pump, a home assistant, or the like) in response to a detection that the user has entered or is entering an extreme diabetic state (e.g., the user is hypoglycemic or hyperglycemic). For example, the mobile device calculates the blood glucose level of the user based on data from the CGM, or receive the blood glucose level of the user from the BGM, and determine that the blood glucose level is above a high-end threshold (e.g., the user is in a hyperglycemic state, or is about to enter the hyperglycemic state) or below a low-end threshold (e.g., the user is in a hypoglycemic state, or is about to enter the hypoglycemic state). The triggering event is detected when the user device receives an indication of a defect or other problem with the user device itself or another user device (e.g., the mobile device 104, the CGM 102, a CGM controller, the BGM 106, or the insulin pump 116, 118). For example, the defect or other problem includes a battery level of the device being below a threshold, a sensor being out of calibration, or the like.

At 204, the user device generates the alert. The user device generates the alert and provide the alert via an auditory signal or as a notification on a screen of the user device. For example, if the user device is a mobile device, the alert is presented by playing a specific sound or tone associated with the alert.

The user device may receive an acknowledgement of the diabetes-related alert from the user at 206. For example, the user may tap the screen of the user device to acknowledge the alert. The user may acknowledge the alert by saying a word or phrase that is detected by a microphone of the user device. If the user has acknowledged the alert, the user device stops the alert and return the volume level of future alerts to a default setting at 212.

If alert is acknowledged at the user device within a predefined period of time, the user device determines whether a maximum volume level (e.g., a predefined total volume level) for the alert has been reached at 208. If the maximum volume level has been reached, the user device delivers the alert again at the same volume level at 204. If the maximum volume has yet to be reached, the user device increases the volume level diabetes-related alert at 210 and provide the diabetes-related alert at the increased volume level at 204.

In some embodiments, the user device increases the volume level of the alert by a just-noticeable difference (JND). A JND is an amount that an intensity level (e.g., a volume level or vibration level) is changed in order for the difference to be detectable at least half the time. For example, the intensity level is a volume level, and a default JND for the volume level is in a range of approximately 0.2 to 0.4 dB. The JND amount is modified by the user device, based on, for example, user-specific criteria, the user's response to previous alerts delivered by the user device, or a condition of the user device. For example, if the user device is in a sleep mode, the JND is approximately 15 dBA. Increasing the alert volume by a JND increases the likelihood that a user will acknowledge a subsequent alert while minimizing battery loss for the user device or noise pollution.

Figure 3:
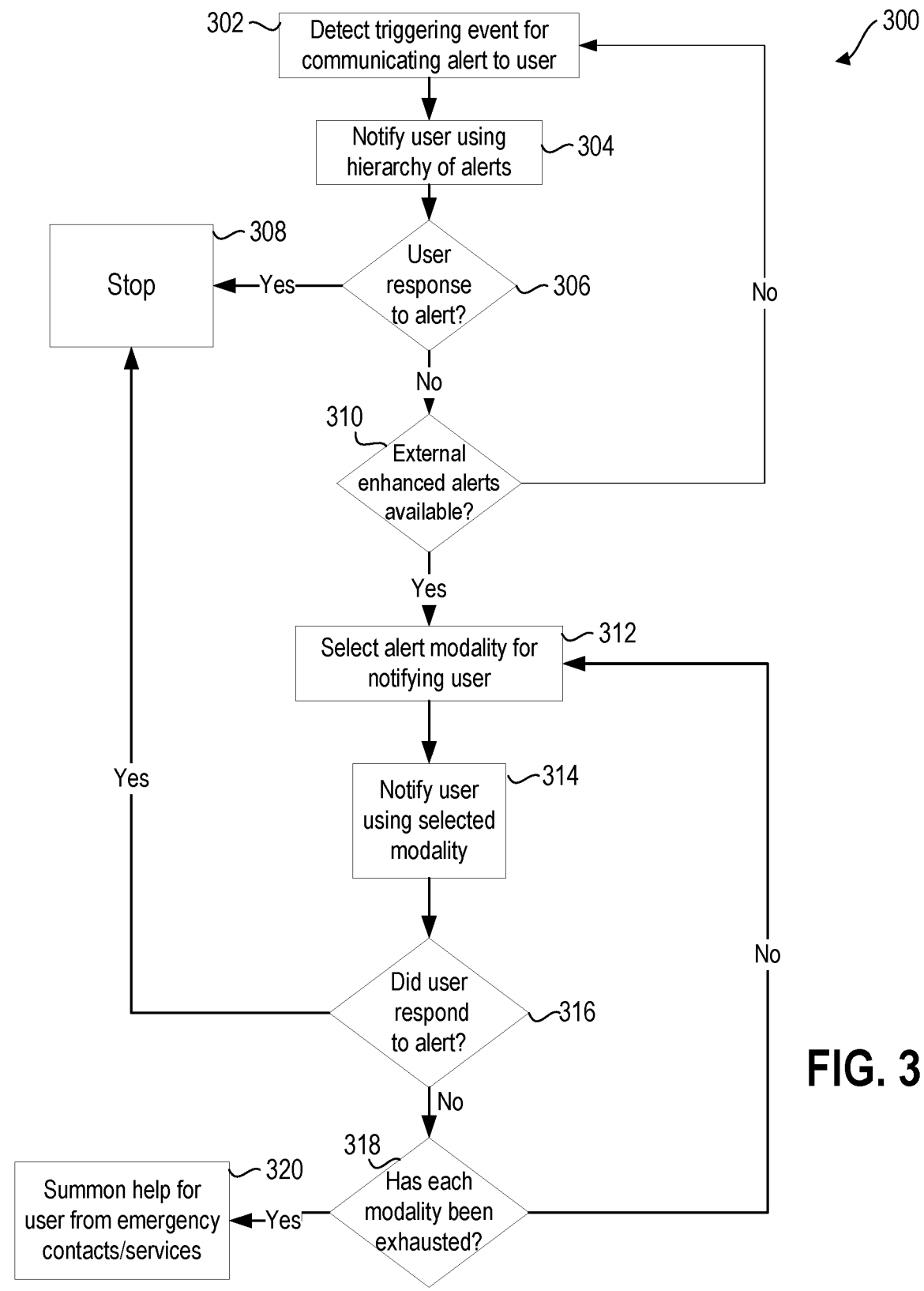
FIG. 3 shows a flowchart of an example process for delivering a diabetes-related alert using different modalities.

FIG. 3 shows a flowchart of an example process 300 for delivering a diabetes-related alert using different modalities. The example process 300 is performed by one or more devices, such as one or more user devices, for example. The process 300 is performed by a single user device, or distributed across multiple devices.

As shown in FIG. 3, the user device detects a triggering event at 302 for communicating a diabetes-related alert to a user. The triggering event is detected as described herein. A user device delivers the alert at 304. The alert is sent using a hierarchy of progressive alert notifications. For example, an alert is delivered to a user as an auditory signal via the user device. If the user device does not receive an acknowledgement of the alert, the user device continues to increase the volume level and repeat the alert until a maximum volume level has been reached (e.g., as shown in FIG. 2). The user device similarly notifies the user using a hierarchy of non-audible alerts, such as increased vibrations of the user device.

Referring again to FIG. 3, the user device determines whether the user acknowledged the alert at 306. The user may fail to acknowledge the alert, because, for example, the user is out of range of the user device, the user is asleep, the maximum alert volume level is too low to be heard given ambient noise, or the like. If the user device provides the diabetes-related alert via a home assistant (e.g., a home automation system or home speaker system), the user may be in a location other than the user's home. If the user device receives an acknowledgement of the alert, the user device stops the alert at 308.

If the user device fails to receive an acknowledgement of the alert after the alert has reached a maximum alert intensity or the alert has been presented a predefined number of times, the user device determines whether an external enhanced alert is allowed at 310. For example, the user device determines whether an external source is available or has been configured for providing alerts from the user device.

If an external enhanced alert is available, a second alert is delivered to the user using a different modality than the initial alert. A modality is, for example, a pre-recorded speech message, an SMS or other text message, a phone call, a visual alert, an alert provided via a home automation system, or the like. The user device selects a modality for the second alert at 312 and configures a message to be sent to the external device for providing the external alert. For example, the user device selects a speech alert message as the modality for the second alert.

In some embodiments, the user device uses information from an integrated accelerometer/gyroscope or GPS circuit to determine which modality should be used for the second alert. For example, the user device is a wearable device, and data from the accelerometer indicates that the user is asleep, and thus unlikely to hear a simple auditory alert. Alternatively, data from the GPS circuit indicates that the user is away from home, and thus unlikely to detect an alert provided by a home assistant.

In some embodiments, the user device forwards the alert to a connected remote computing device via a wireless network. For example, the remote computing device is a virtual assistant. The remote computing device or the user device then delivers the second alert to the user using the selected modality at 314. For example, the virtual assistant device delivers the alert as a speech alert message notifying the user of the alert condition.

The user device determines whether the user acknowledged the second alert at 316. If the user fails to acknowledge the second alert within a predefined time period or after the alert has been presented a predefined number of times, the user device determines whether each modality has been used (e.g., modalities are exhausted) at 318. If there is at least one modality that is available to the user device, the user device selects another modality at 312 and alerts the user using the selected modality. For example, if the user does not acknowledge the second alert, the user device calls the user's phone number(s) via a telecommunication network and delivers a pre-recorded alert notification, sends a predefined text message via a telecommunication network, or sends a predefined message via an instant messaging service or a communication application (e.g., Skype, WhatsApp, iMessage, or the like) to another computing device, such as a phone or computer.

The user device continues to select different modalities and deliver the alert to the user using the different modalities if the user continues to fail to acknowledge the alert. For example, the user device sends a message configured to control a smart home automation system (e.g., a home assistant), which delivers the alert by changing the state of one or more objects in the user's home (e.g., flashing lights, moving window blinds, or the like). For example, the home automation system controls a diabetes notification lamp and instructs the diabetes notification lamp to deliver the alert.

In some embodiments, the user device determines the modalities for the alert based on a priority level associated with the triggering event of the diabetes-related alert. There is a hierarchy of modalities from a lowest priority to a highest priority. The lowest priority modality for the alert is a least intrusive and the alerts become more intrusive until the highest priority alert. A highest priority modality is also selected, and the priority level decreases to a lowest priority modality after the alert has been provided for a predefined period of time or a predefined number of times. The priority level of is based on the triggering event. For example, if the triggering event indicates a relatively minor issue (e.g., the user's blood glucose level is higher than normal, but still within a safe range), the priority level of the alert is lower than the priority level of an alert when the triggering event indicates a relatively major issue (e.g., the user's blood glucose level indicates the user is in an extreme diabetic state). The increased priority level increases the number of modalities that are used to provide the alert, the volume level of the alert, or otherwise increases the severity of the alert.

If the user device has exhausted the available modalities, the user device sends a message to the user's emergency contact or an emergency service at 320. The emergency contacts are preselected by the user and the user device contains contact information for the emergency contacts. The message is, for example, an SMS or other text message, a prerecorded voice message, or the like. If the user fails to acknowledge the alert within a predetermined time period after the emergency contacts have been contacted, or if the alert condition is time-sensitive, the user device contacts emergency services and directs them to the user's last known location at 320.

Figure 4:
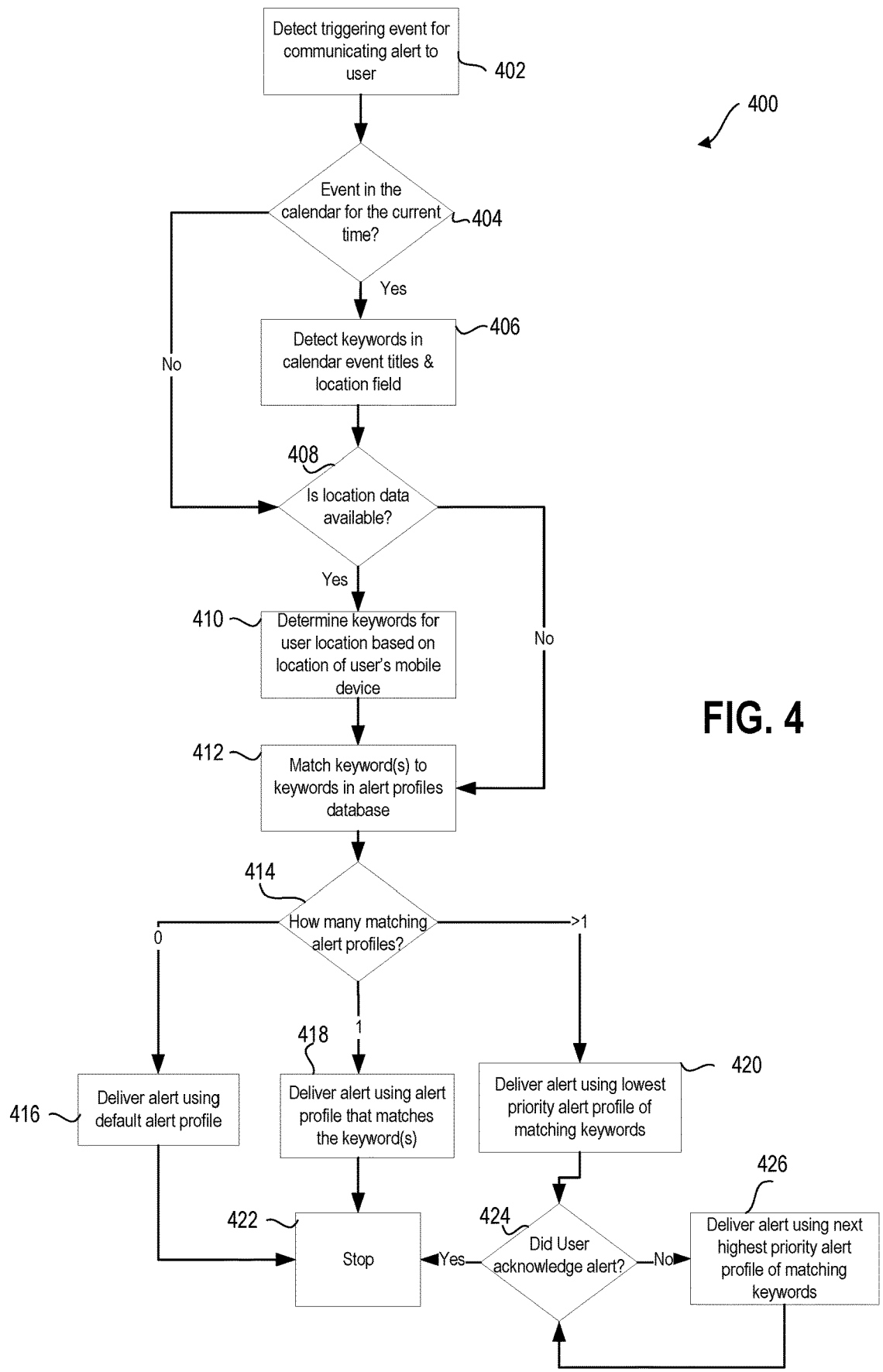
FIG. 4 shows a flowchart of an example process for delivering a diabetes-related alert using information from a user's calendar and a location of the user.

FIG. 4 shows a flowchart of an example process 400 for delivering a diabetes-related alert using information from a user's calendar and a location of the user. The example process 400 is performed by one or more devices, such as one or more user devices, for example. The process 400 is performed by a single user device, or distributed across multiple devices.

The user may be in a location or at an event where a modified alert volume is preferable. For example, the user may be in a location or at an event where certain alerts (e.g., having loud noises) are socially inappropriate or otherwise discouraged. Presenting an alert at a default volume level may interrupt the event or embarrass the user. The user may disable the alert or decrease the volume of future alerts, which may cause the user to miss future alerts. Alternatively, the user may be in a location or at an event where the ambient noise volume level is higher than normal, which may cause the user to miss an alert at the default volume level. If the alert is provided at a level that is unnoticeable to the user, the battery power of the user device is unnecessarily reduced, which may cause the user device to lose power and be unable to alert the user of further events.

In some embodiments, the user device determines an appropriate alert profile for an alert based on information in the user's calendar or geographic data. As illustrated in FIG. 4, the user device detects a triggering event at 402 for communicating an alert to the user. In response to detecting the triggering event, the user device determines whether the user has previously given permission to access the user's personal calendar. If the user has given permission to access their personal calendar, the user device determines whether there is an event in the calendar for the current time or within a predefined period of time at 404. For example, upon detection of a triggering event, the user device accesses the user's calendar and determine that there is an event for the current time or within a predefined period of time. The calendar is accessed by the user device locally, from a remote datastore, from a remote computing device, or from a calendar service. If there is no event in the calendar at the current time or within a predefined period of time, or if the user has not given permission to access the calendar, the user device proceeds to 408.

If there is an event in the calendar at the current time or within a predefined period of time, the user device detects one or more keywords in the title field of the event or in the location field of the event at 406. For example, the event title is "Ravens game" and the event location is "M&T Bank Stadium". The user device detects the keyword "game" in the title field or the keyword "stadium" in the location field. If the location is a street address, the user device attempts to match the street address to a known entity (e.g., a business, residence, or other entity) at that street address and detect keywords in the name of the known entity. The name of the known entity is a friendly name. For example, if the location is the street address "1101 Russell Street", the user device determines that the known entity at that street address is "M&T Bank Stadium" and uses the keyword "stadium" for the location field.

At 408, the user device determines whether location data (e.g., GPS data) is available to the user device. Location data may not be available to the user device if, for example, the user device is not in range of a GPS signal, or the user has not given permission to use location-based services or access their location. If the location data is unavailable, the user device proceeds to 412. If the location data is available, the user device determines one or more keywords for the user location based on the location data. For example, the data indicates the location of the user device as a set of latitude and longitude coordinates. The user device uses a location database to match the coordinates to an address. The user device uses the street address to determine one or more keywords for a known entity at that address. For example, the user device obtains its latitude and longitude coordinates from GPS data, and determines that the street address matching those coordinates is "1101 Russell Street." If the known entity found at the street address has one or more metadata fields that are useful to categorizing the type of event or location at that known entity in its GPS database information, the user device detects keywords in the metadata fields. For example, known entity "M&T Bank Stadium" at street address "1101 Russell Street" may have one or more metadata fields indicating it is used for football events, and the user device detects the keyword "football" or "sports" in the metadata fields.

At 412, the user device matches the keywords from the calendar or the geographic location data to keywords associated with pre-determined alert profiles. The alert profiles are stored in an alert profile database on the user device, an external device, or an external datastore. The alert profiles are associated with one or more keywords. For example, the user device searches available alert profiles that are associated with the keywords "game," "stadium," "football," or "sports."

At 414, the user device determines how many keywords from the calendar or the geographic location data matched keywords associated with the alert profiles. If no keywords matched, the user device delivers the alert using a default alert profile at 416 and stops at 422. If one or more of the keywords matched to one alert profile, the user device delivers the alert using the alert profile that matches the keywords at 418 and stops at 422. For example, the user device determines that one or more of the keywords "game," "stadium," "football," and "sports" matched the alert profile "sporting event." The user device delivers the alert using the alert profile for "sporting event."

If one or more of the keywords matched to more than one alert profile, the user device delivers the alert using the lowest priority alert profile that matches the keywords at 420. For example, the user device determines that one or more of the keywords "game," "stadium," "football," or "sports" matched the alert profiles for "sporting event" and "practice." The user device determines that the alert profile for "practice" is lower priority than the alert profile for "sporting event." For example, the "practice" alert profile uses vibration and an auditory signal at a low volume, and the "sporting event" alert profile uses vibration and an auditory signal at a high volume level. The higher priority alert profile uses more alerts, or is more severe (e.g., louder) to get the user's attention more quickly during higher priority triggering events. The user device delivers the alert using the alert profile for "practice." Alternatively, the user indicates a selection of a global alert type for delivering alerts to the user. The user devices use the global alert type to deliver the alert to the user.

In some embodiments, the user device determines whether a user acknowledgement was received in response to the alert using the lowest priority alert profile at 424. If the user acknowledged the alert, the user device stops at 422. If the user failed to acknowledge the alert, the user device delivers the alert at the next highest priority alert profile at 426. For example, if the user failed to acknowledge the alert using the "practice" alert profile, the user device delivers the alert using the "sporting event" alert profile.

The user device continues to deliver the alert using remaining matching alert profiles as long as the user fails to acknowledge the alert. If the user device has delivered the alert using each of the matching alert profiles, the user device repeats the alert using the highest priority alert profile. For example, if the user fails to acknowledge the alert using the "practice" alert profile and the "sporting event" alert profile, the user device repeatedly delivers the alert using the "sporting event" alert profile until the user acknowledges the alert, or until a predefined period of time or number of repetitions of the alert.

A lower priority alert profile is an alert profile that has a quieter volume level or a lower number of sensory channels. A non-auditory alert is lower priority than an auditory alert. For example, an alert that uses vibration is lower priority than an alert that uses vibration and an auditory signal, and an alert that uses an auditory signal at a lower volume level is lower priority than an alert that uses an auditory signal at a higher volume level. Locations or events that have a lower priority alert profile include, but are not limited to: a movie theater, an artistic performance, a library, a museum, a religious building or service, a wedding or funeral, a business meeting, or a practice. Locations or events that have a higher priority alert profile include, but are not limited to: a gathering, a restaurant, the user's home, or an office or workplace. Locations or events that have an even higher priority alert profile include, but are not limited to: a game or other sporting event, a fair, a concert, a conference, or a market.

Figure 5:
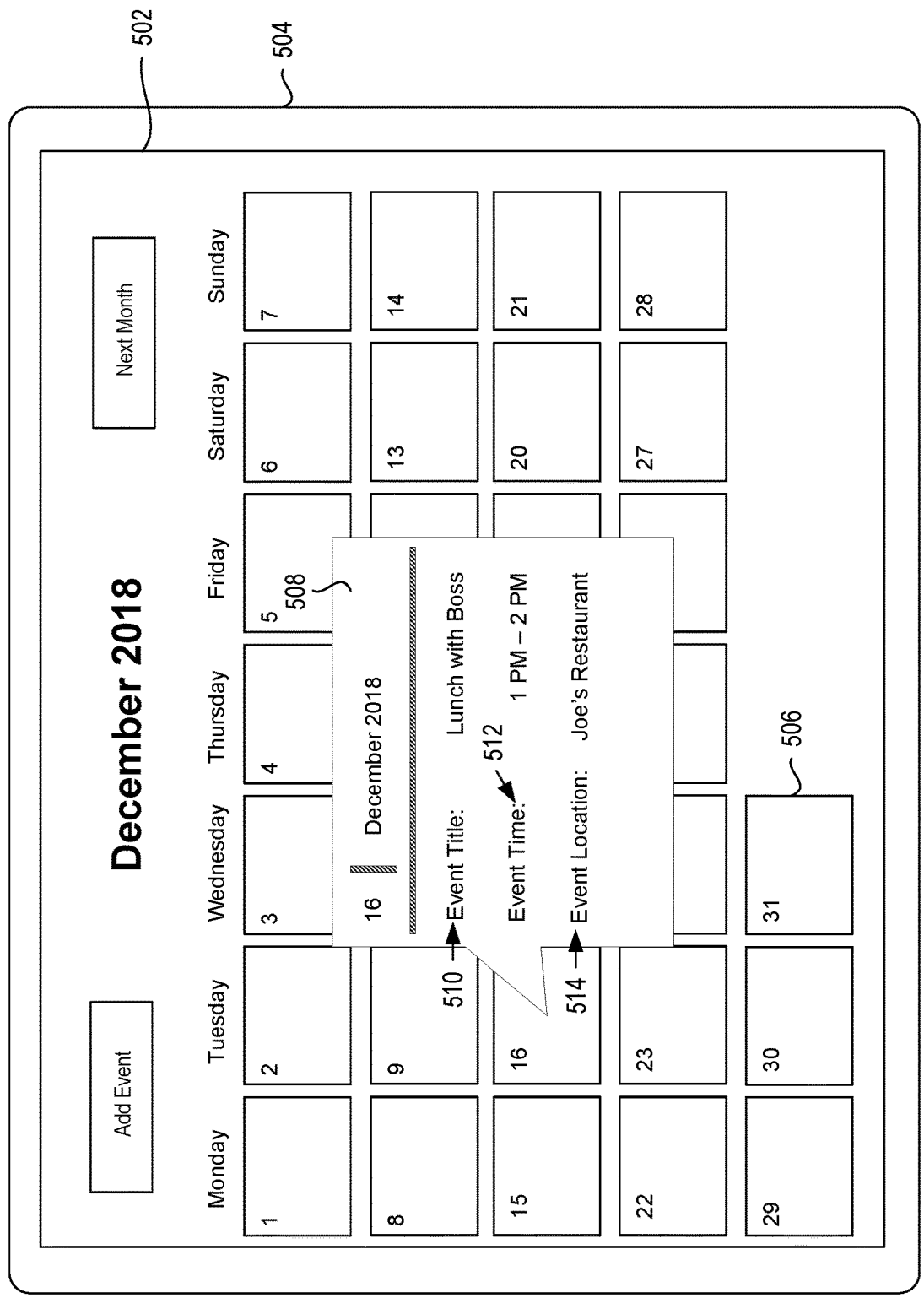
FIG. 5 shows an example graphical user interface (GUI) that displays calendar information used to determine the location of a user.

FIG. 5 shows an example graphical user interface (GUI) 502 that displays calendar information used to determine the location of a user. For example, the GUI 502 is displayed on user device 504. User device 504 is any user device with a display that is capable of accessing calendar information.

For example, user device 504 is a smartphone, a wearable device, a laptop, a tablet, a BGM, a CGM controller, or the like.

The GUI 502 displays a calendar 506. The calendar 506 is shown including hours, days, months, and the like. The GUI 502 displays a popup 508 that displays information about a specific calendar event. The information includes the event title 510, the event time 512, or the event location 514. The user device 504 uses the event time 512 to determine whether there is a current event at the time an alert triggering event is detected and whether the event is occurring in a predefined period of time. The user device 504 uses the event title 510 or the event location 514 to determine keywords for the event. The user device 504 matches the keywords to one or more alert profiles for presenting the alert as described herein.

For example, the user device 504 detects a triggering event at 1:30 PM on December 16$^{th}$. The user device 504 accesses the user's calendar 506 and determines that the user has one event on the calendar 506 for December 16$^{th}$. The user device 504 determines from the event time 512 that the event is currently occurring, or is occurring in a predefined period of time. The user device 504 detects the keyword "lunch" in the event title 510 and the keyword "restaurant" in the event location 514. The user device 504 matches the keywords "lunch" or "restaurant" to the alert profile "Restaurant" and delivers the alert using the "Restaurant" alert profile.

Figure 6:
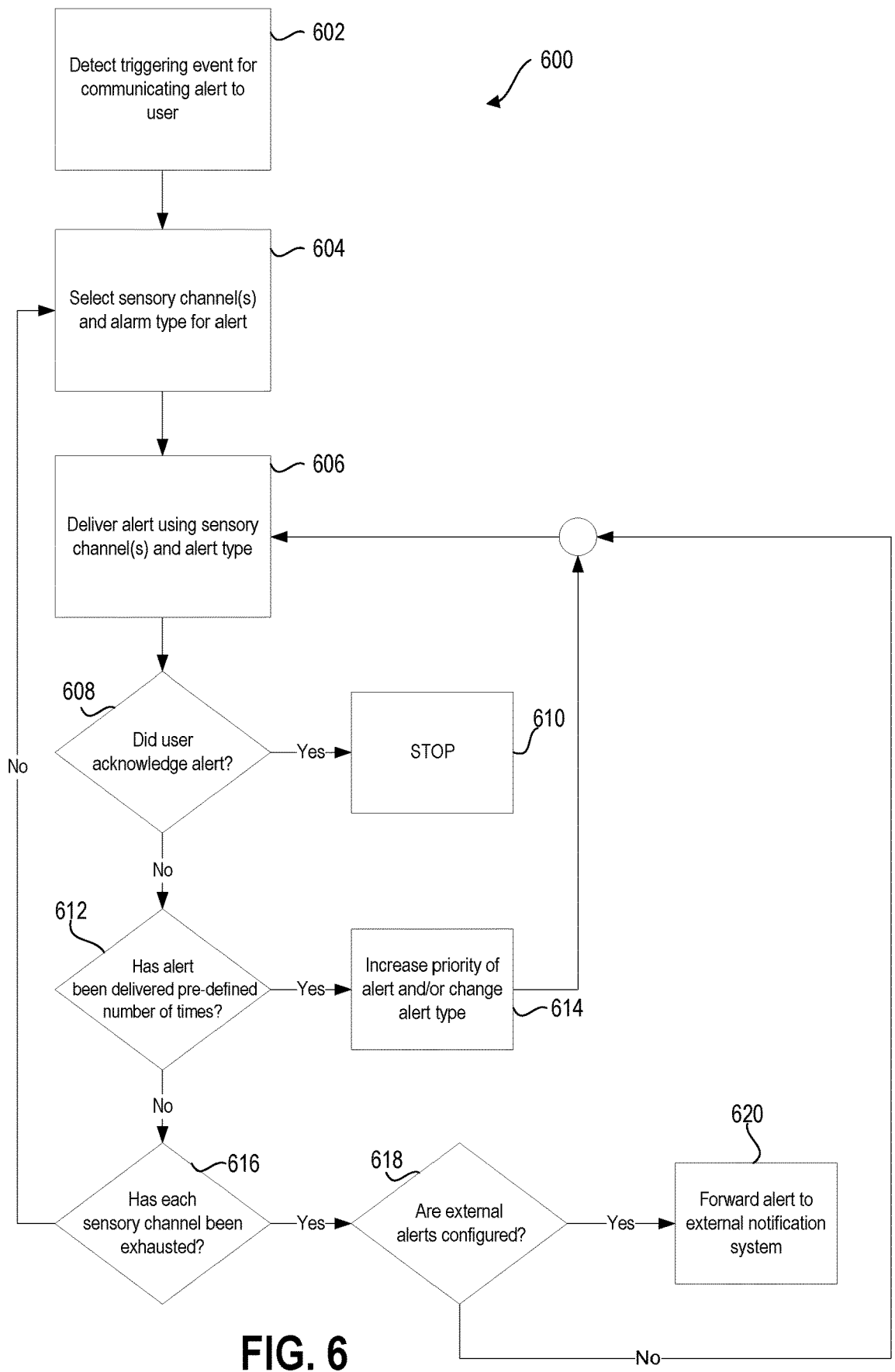
FIG. 6 shows a flowchart of an example process for providing a diabetes-related alert to a user using different sensory channels.

FIG. 6 shows a flowchart of an example process 600 for providing a diabetes-related alert to a user using different sensory channels. The example process 600 is performed by one or more devices, such as one or more user devices, for example. The process 600 is performed by a single user device, or distributed across multiple devices.

A sensory channel is a visual channel, an auditory channel, a haptic signal, another sensory channel, or a combination thereof. There are one or more distinct alert types within a given sensory channel. For example, the alert is provided via the visual sensory channel by displaying a message on a display of a user device, turning on or flashing an LED on the user device, turning on or flashing a flashlight (e.g., a photo flash) of the user device, controlling another device in the user's environment (e.g., an LED, window blinds, or a speaker device), or otherwise performing a visual control.

In some embodiments, the alert is provided via the auditory channel by playing an audible alert. The audible alert includes a speech alert that includes an audible spoken version of the alert message (e.g., via a text-to-speech service or pre-recorded speech), an auditory alert notification (e.g., a chime, a tone, a beep, or an alarm) or the like. For example, an alert provided via the auditory channel includes the user's name. An auditory alert is provided by the user device or by another device in the user's environment (e.g., earphones, a speaker device, a home automation device, an alarm system, or the like).

There is a hierarchy of sensory channels from a lowest priority to a highest priority and a similar hierarchy of alert types within a single sensory channel. For example, a haptic channel is lower priority than a visual channel, and a visual channel is lower priority than an auditory signal. A hierarchy of sensory channels from lowest priority to highest priority is haptic, visual, and auditory, though the levels of priority may be different.

Within each sensory channel, there is a priority level associated with each type of alert. For example, within the visual channel, an alert presented on a display of the user device is lower priority than flashing an LED of the user device. Within the auditory channel, a speech alert is lower priority than an auditory alert notification. An auditory alert at a lower volume is lower priority than an auditory alert at a higher volume.

In some embodiments, an alert initially has a lower priority level, and is delivered using a sensory channel and alert type commensurate with the lower priority level. If the user fails to acknowledge the initial alert, the priority level of the alert increases. As the priority level of an alert increases, the intensity of the alert within a sensory channel increases (e.g., a volume of an auditory alert is increased, the vibration increases, the brightness/flashing of a display or LED increases), a combination of alert types within a sensory channel is changed (e.g., a flashing LED is used in addition to an alert message on a display), another higher priority sensory channel is used (e.g., an auditory alert is used instead of a visual alert), or a combination of sensory channels is changed (e.g., a sensory channel is added). The priority level of the alert further increases each time the user fails to acknowledge the alert at a given priority level.

At 602, the user device detects a triggering event for communicating an alert to the user. The triggering event is detected as described herein. The user device selects one or more sensory channels for the alert notification at 604. If there are multiple alert types within the selected sensory channels, the user device selects one or more alert types. The user device selects a lower priority sensory channel or a lower priority alert type for initial presentation of an alert. The user device selects successively higher priority sensory channels or alert types for subsequent deliveries of the alert. The user device delivers the alert to the user using the selected sensory channel(s) and alert type(s) at 606. For example, the initial alert is presented using a first non-audible alert on the user device, such as a vibration of the user device or an onscreen alert notification (e.g., an alert message) on the display of the user device.

At 608, the user device determines whether a user acknowledgement is received for the alert. If the user acknowledged the alert, the user device stops at 610. If the user does not acknowledge the alert, the user device determines at 612 whether the alert has been delivered a pre-defined number of times, or for a predefined period of time, using the selected sensory channel(s). If the alert has failed to be delivered the pre-defined number of times using the selected sensory channel(s), the user device increases the priority of the alert or selects a different alert type at 614. Lower priority alerts are a lower intensity level than higher priority alerts. The different alert type is used as a replacement for, or in addition to, the initial alert type. The different alert type has a higher priority (e.g., is less discreet) than the initial alert type. The user device delivers the alert using the higher priority alert (e.g., having increased intensity) at the selected alert type at 606. For example, the user device delivers the alert by providing a second non-audible alert having a higher priority than the first non-audible alert, such as by flashing an LED of the user device in addition to vibrating the user device and displaying the on-screen alert. The priority is increased by providing additional alerts.

If the alert has been delivered the pre-determined number of times using the selected sensory channels or for a pre-defined period of time, the user device determines whether each sensory channel has been used by the user device to deliver the alert at 616. If one or more sensory channels has not been used, the user device selects a different sensory channel to deliver the alert at 604. The different sensory channel is used as a replacement for or in addition to the initial sensory channel. The different sensory channel has a higher priority (e.g., is less discreet) than the initial sensory channel. For example, the user device selects an auditory channel to deliver the alert in addition to the haptic channel or the visual channel. For example, if the user fails to acknowledge the second non-audible alert, the user device delivers the alert at 606 via the auditory channel. The user device delivers the alert by providing a first audible alert having a higher priority than the second non-audible alert. For example, the user device delivers the first audible alert by providing an audible version of the alert message read at a first volume level via a speaker of the user device using a text-to-speech service in addition to displaying the on-screen alert and vibrating the user device. The alert message is pre-recorded and includes the user's name.

The user device continues to increase the intensity of the alert or change the alert type at 614 if the user device determines that the user did not acknowledge the alert at 608 and that the alert has been delivered the pre-defined number of times at 612. If the user fails to respond to the first audible alert, the user device delivers the alert by providing a second audible alert having a higher priority than the first audible alert. For example, the user device delivers the second audible alert by providing an auditory alert notification at a first volume level via a speaker of the user device in addition to displaying the on-screen alert or vibrating the user device. If the user fails to acknowledge the second audible alert, the priority level of the alert is increased by, for example, providing additional alert types or by increasing the volume level of the alert. The intensity level of the alert continues to increase until the user acknowledges the alert.

If the alert has been delivered the pre-defined number of times using the selected sensory channels and each sensory channel has been used to deliver the alert, the user device determines whether external alerts are configured. If external alerts are configured, the user device forwards the alert to an external alert system, which delivers the alert as described herein. If external alerts are not configured, the user device continues to deliver the alert using the lowest priority sensory channel(s) and alert type(s).

In some embodiments, the user device determines that one or more sensory channels are unavailable based on, for example, a characteristic of the user, a time of day, or the like. For example, if the user is deaf or otherwise has hearing problems, the user device determines that the auditory channel is unavailable for delivering the alert. If the time of day indicates that the user is most likely asleep, the user device determines that the user is unlikely to acknowledge an alert sent using a visual channel, and determines that the visual channel is unavailable for delivering the alert. Similarly, the user device determines that the user is unlikely to acknowledge one or more alert types within a sensory channel, and determines that the alert types are unavailable for delivering the alert.

Figure 7:
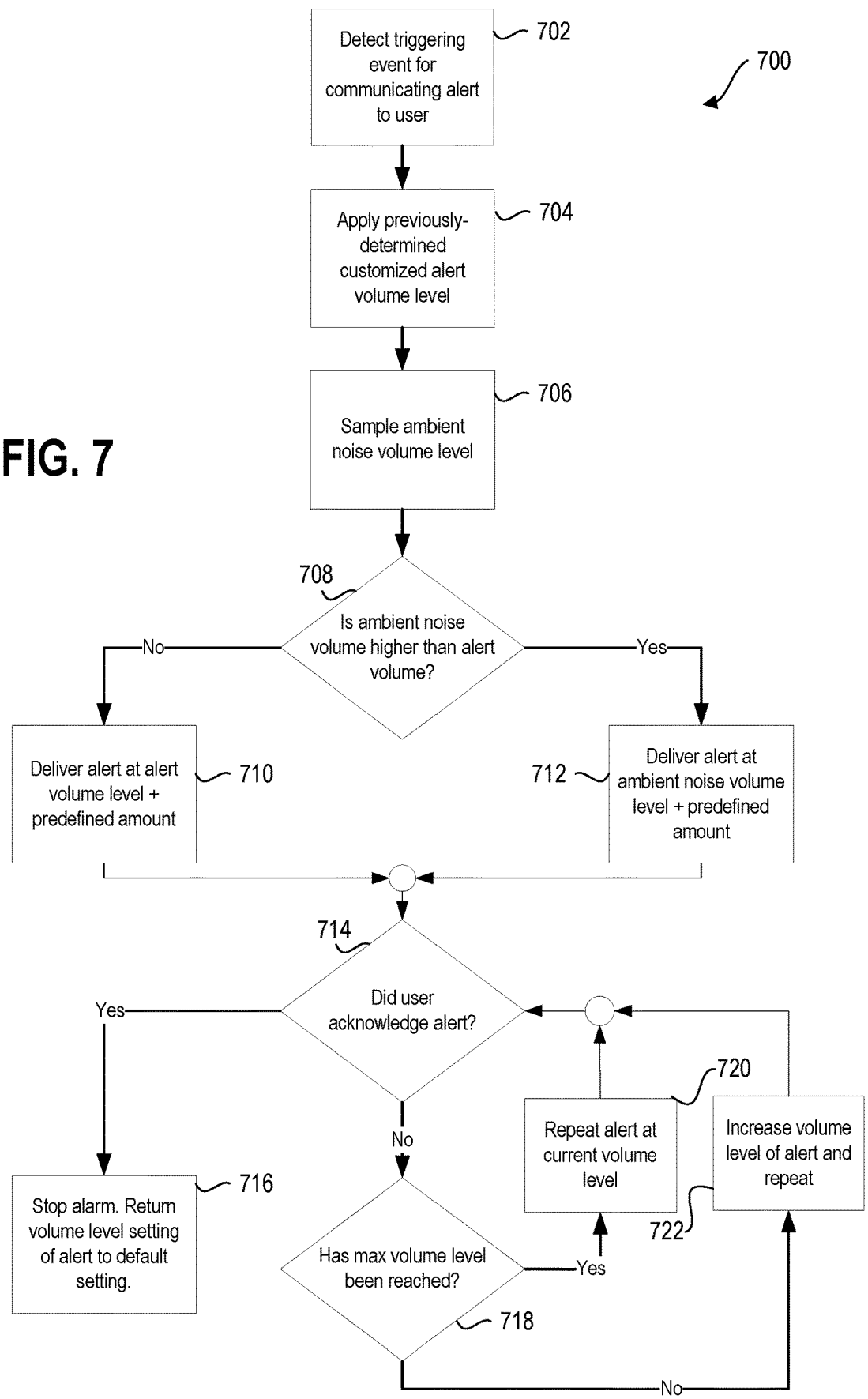
FIG. 7 is a flowchart of an example process for determining a volume level of an alert based on an ambient noise volume level.

FIG. 7 is a flowchart of an example process 700 for determining a volume level of an alert based on an ambient noise volume level. The example process 700 is performed by one or more devices, such as one or more user devices, for example. The process 700 is performed by a single user device, or distributed across multiple devices.

At 702, the user device detects a triggering event for communicating an alert to the user. The alert is an auditory signal. At 704, the user device applies a previously-determined volume level to the alert. The previously-determined volume level is customized to the user based on, for example, the user's gender or age. The previously-determined alert volume level, taking into account the age and gender of the user, is, for example, 60 dBA. The user device samples an ambient noise volume level at 706 using a microphone of the user device. The user device samples the ambient noise volume level by testing a sound pressure level, which is measured in dBA. The user device samples the ambient noise volume level using a microphone and determines that the ambient noise volume level is, for example, approximately 55 dBA.

The user device determines whether the ambient noise volume level is higher than the previously-determined volume level at 708. If the ambient noise volume level is not higher than (e.g., less than or equal to) the previously-determined volume level, the user device adds a predetermined amount to the previously-determined volume level and deliver the alert using the increased volume level at 710. The predetermined amount to be added to the alert volume is, for example, 10 dBA. For example, if the previously-determined alert volume level is 60 dBA and the ambient noise volume level is 55 dBA, the user device adds 10 dBA to the previously-determined volume level and deliver the alert at 70 dBA.

If the ambient noise volume level is higher than the previously-determined volume level, the user device adds a predetermined amount to the ambient noise volume level and deliver the alert at the increased volume level at 712. For example, if the ambient noise level is 75 dBA and the predetermined amount is 10 dBA, the user device delivers the alert at 85 dBA.

At 714, the user device determines whether the user acknowledged the alert. If the user acknowledged the alert, the user device stops the alert and return the volume level setting of future alerts to a default setting at 716. The default setting is the previously-determined volume level. If the user did not acknowledge the alert, the user device determines whether a maximum volume level has been reached at 718. If the maximum volume level has been reached, the user device repeats the alert at the maximum volume level at 720, and returns to 714.

If the maximum volume level has not been reached, the user device increases the volume level of the alert, repeats the alert at 722, and returns to 714. For example, if the user does not acknowledge an initial 75 dBA alert, the user device increases the volume of the alert by a previously-determined amount (e.g., 5 dBA) and delivers the alert at the updated volume level (e.g., 80 dBA). If the user continues to fail to acknowledge the alert, the user device continues to increase the volume of the alert by the predetermined amount until reaching the maximum volume level. For example, if the maximum volume level of the alert is 100 dBA, the user device delivers an initial alert at 75 dBA, followed by 80 dBA, 85 dBA, 90 dBA, 95 dBA, and 100 dBA. The user device continues to deliver the alert at the maximum volume level if the user continues to fail to acknowledge the alert.

Figure 8:
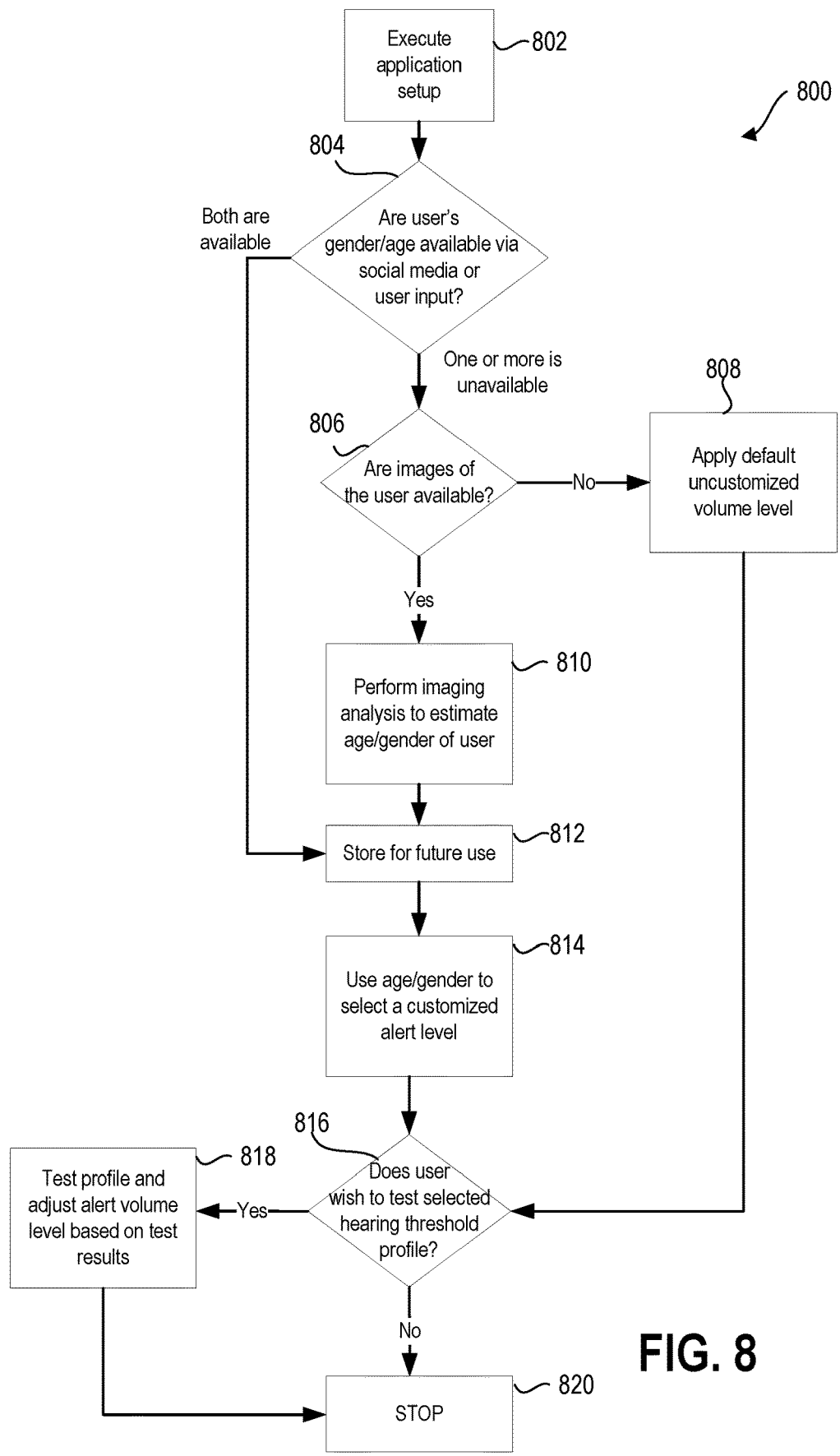
FIG. 8 shows a flowchart of an example process for determining a volume level of an alert based on user-specific criteria (e.g., an age or gender of a user).

FIG. 8 shows a flowchart of an example process 800 for determining a volume level of an alert based on user-specific criteria (e.g., an age or gender of a user). The example process 800 is performed by one or more devices, such as one or more user devices, for example. The process 800 is performed by a single user device, or distributed across multiple devices.

The user's ability to detect an alert may be decreased because of age-related sensory loss. For example, an older user is less likely than a younger user to detect an auditory alert at a given volume. Similarly, an older user is less likely than a younger user to detect and read an on-screen alert at a given brightness. In addition, a user's gender may affect how their sensory loss progresses with age. For example, men may experience hearing problems beginning earlier than women, and hearing loss may progress faster in men than in women. Customizing an alert based on a user's age or gender makes it more likely that the user will detect the alert, and therefore allows the user to correct the condition that caused the alert earlier. This prevents unnecessary battery loss for the user device by providing alerts that are undetectable to the user.

At 802, an application setup is executed on the user device (e.g., when the application is opened for the first time or at later configuration). The application interacts with the user device to detect alert conditions and deliver alerts to the user. At 804, the user device determines whether the user's age (e.g., or birthdate) or gender are available to the application. For example, the age or gender is available locally, via a datastore, via user input, or via a remote computing device (e.g., social media portal accessible on a remote server, government web portal accessible on a remote server, or another remote device from which age and gender information is accessed).

The user may enter their age or gender into the application. For example, the user may input that they are male and 59 years old. Alternatively, the user device has access to a social media profile of the user (e.g., Facebook, AppleID, a contact card for the user, a Health App, or the like) that includes the user's age or gender. The user input or social media profile may provide the user's birthdate, and the user device calculates the user's age from the user's birthdate and the present date. For example, if the user enters the birthdate May 12, 1959 into the app and the present date is Jan. 1, 2019, the app determines that the user is 59 years old. The profile may have a profile photo of the user, and the user device determines the user's age or gender (e.g., using a machine learning algorithm) using imaging analysis based on the profile photo. The algorithm or imaging analysis compares portions of the profile photo of the user or features in the profile photo of the user with predefined images for which age information is known or determined. For example, the algorithm or imaging analysis identifies facial features (e.g., pupils, nose, nose tip, mouth, eyebrows, lips, or other features) and compares the features to the features in the photos for which the age information is known or determined. When machine learning algorithms are employed, a different model is built to determine gender and age. The algorithm looks at quantifiable features in the photos and uses a regression model to model the resulting ages.

If both the user's age and the user's gender are available to the user device, the user device stores the user's age and gender for future use at 812. The user device updates the user's age as the user's age increases with time. For example, if the user device has the user's birthdate, the user device increments the user's age every year on their birthday. If the user device has the user's age but not their birthdate, the user device increments the user's age on, for example, January 1 of every year.

If one or more of the user's age or gender is unavailable, the user device determines whether images of the user are available to the user device at 806. For example, the user device determines whether it has access to a camera roll of the user device, and whether there are any images (e.g., selfies) of the user within the camera roll. The user device determines that a most commonly-occurring face in the camera roll is the user's face, or the user is indicated in metadata associated with the image.

If there are no pictures of the user in the camera roll, or if the user device does not have access to the camera roll, the user device applies a default non-customized volume level (e.g., 70 dBA) to any future alerts at 808 and proceeds to determine whether the user wishes to test the default volume level at 816. If there are images of the user available to the user device, the user device performs an imaging analysis on the images of the user at 810 to estimate the age or gender of the user. The user device stores the user's estimated age or gender for future use at 812 and uses the age and gender to select a customized alert level (e.g., 80 dBA) at 814. For example, the user device sets the customized alert level to be higher than the default volume level if the user is older than average.

At 816, the user device determines whether the user wishes to test the selected alert level. If the user wishes to test the selected alert level, the user device presents a hearing threshold test to the user at 818. For example, the hearing threshold test is used to determine the user's absolute hearing threshold (e.g., a minimum amount of sounds stimulation required for the user to detect the sound stimulus 50 percent of the time). The hearing test includes instructing the user to sit in a quiet area, presenting gradually increasing (e.g., or decreasing) alert sounds at one or more frequencies and instructing the user to respond when the user hears the alert (e.g., or stops hearing the alert). The selected alert level is modified based on the results of the hearing test. For example, if the user's absolute hearing threshold is 85 dBA at 5000 Hz at an ambient noise level of 70 dBA, the user device modifies the selected alert volume level to have a baseline of 85 dBA.

Figure 9:
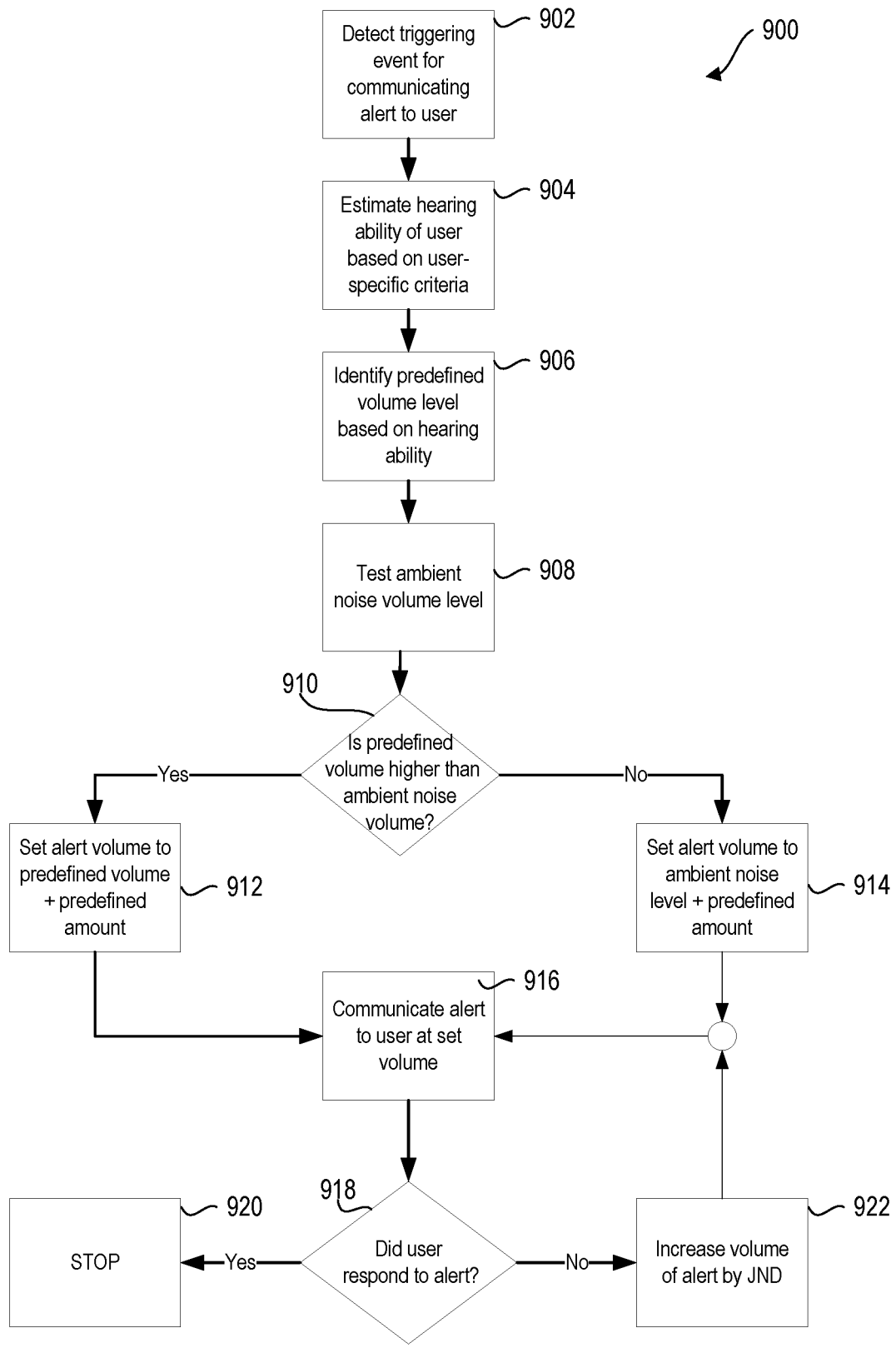
FIG. 9 shows a flowchart of an example process for determining a volume level of an alert based on an ambient noise volume level and a hearing ability of a user.

FIG. 9 shows a flowchart of an example process 900 for determining a volume level of an alert based on an ambient noise volume level and a hearing ability of a user. The example process 900 is performed by one or more devices, such as one or more user devices, for example. The process 900 is performed by a single user device, or distributed across multiple devices.

At 902, the user device detects a triggering event for communicating an alert to the user. At 904, a hearing ability of the user is estimated. The hearing ability is estimated based on user-specific criteria (e.g., an age or gender of the user, a physical condition of the user, a mental condition of the user, or the like). For example, the user device estimates the hearing ability of the user to be lower if the user is older than average or if the user has hearing impairment. The user's age or gender is determined as described for FIG. 8.

Referring again to FIG. 9, the user device identifies a predefined volume level based on the user's estimated hearing ability at 906. If the user's hearing ability is estimated to be lower than average, the user device identifies a predefined volume level that is higher than a baseline volume level. For example, the baseline volume level is 60 dBA, and the identified volume level is 70 dBA.

The user device samples an ambient noise volume level at 908 using a microphone of the user device. The user device samples the ambient noise volume level by testing a sound pressure level, which is measured in dBA. The user device samples the ambient noise volume level using a microphone and determines that the ambient noise volume level is, for example, approximately 60 dBA.

The user device determines whether the ambient noise volume level is higher than the predefined volume level at 910. If the ambient noise volume level is not higher than (e.g., less than or equal to) the predefined volume level, the user device adds a predetermined amount to the predefined volume level and set the alert volume to be the increased volume level at 912. The predetermined amount to be added to the predefined volume level is, for example, 10 dBA. For example, if the predefined volume level is 70 dBA and the ambient noise volume level is 60 dBA, the user device adds 10 dBA to the predefined volume level and set the alert volume to be 80 dBA.

If the ambient noise volume level is higher than the identified volume level, the user device adds a predetermined amount to the ambient noise volume level and set the alert volume to be the increased volume level at 914. For example, if the predefined volume level is 70 dBA and the ambient noise level is 75 dBA, the user device adds 10 dBA to the ambient noise level and set the alert volume to be 85 dBA.

At 916, the user device delivers the alert to the user at the set alert volume. At 918, the user device determines whether the user acknowledged the alert. If the user acknowledged the alert, the user device stops the alert and returns the volume level setting of future alerts to a default setting at 920. The default setting is the predefined volume level.

If the user did not acknowledge the alert, the user device increases the volume level of the alert by a just-noticeable difference (JND) at 922. A JND is an amount that an intensity level (e.g., a volume level) is changed in order for the difference to be detectable at least half the time. For example, the intensity level is a volume level, and a default JND for the volume level is in a range of approximately 0.2 to 0.4 dB. The JND amount is modified by the user device, based on, for example, the user-specific criteria, the user's response to previous alerts delivered by the user device, or a condition of the user device. For example, if the user device is in a sleep mode, the JND is approximately 15 dBA. Increasing the alert volume by a JND increases the likelihood that a user will acknowledge a subsequent alert while minimizing battery loss for the user device and noise pollution.

The user device sets the alert volume to the increased volume level and deliver the alert at 916. For example, if the initial alert volume was 80 dBA and the JND is 0.5 dBA, the user device delivers a second alert at 80.5 dBA. The user device continues to increase the alert volume by a JND and delivers the alert using the increased alert volume until the user acknowledges the alert or a maximum volume is reached. For example, if the maximum volume level of the alert is 100 dBA, the user device delivers the alert at increments of 0.5 dBA until the alert volume reaches 100 dBA. The user device continues to deliver the alert at the maximum volume level if the user continues to fail to acknowledge the alert. The user device may receive an indication from a second user associated with a healthcare provider. The indications indicate that the user device prevents the user from changing the volume level. For example, the indication indicates that the user device disables a change to control of the volume level by the user. The user device, upon receipt of the indication, disallows the user from preventing the volume level from continuing to increase until the maximum volume (e.g., a predefined total volume level) is met.

Figure 10:
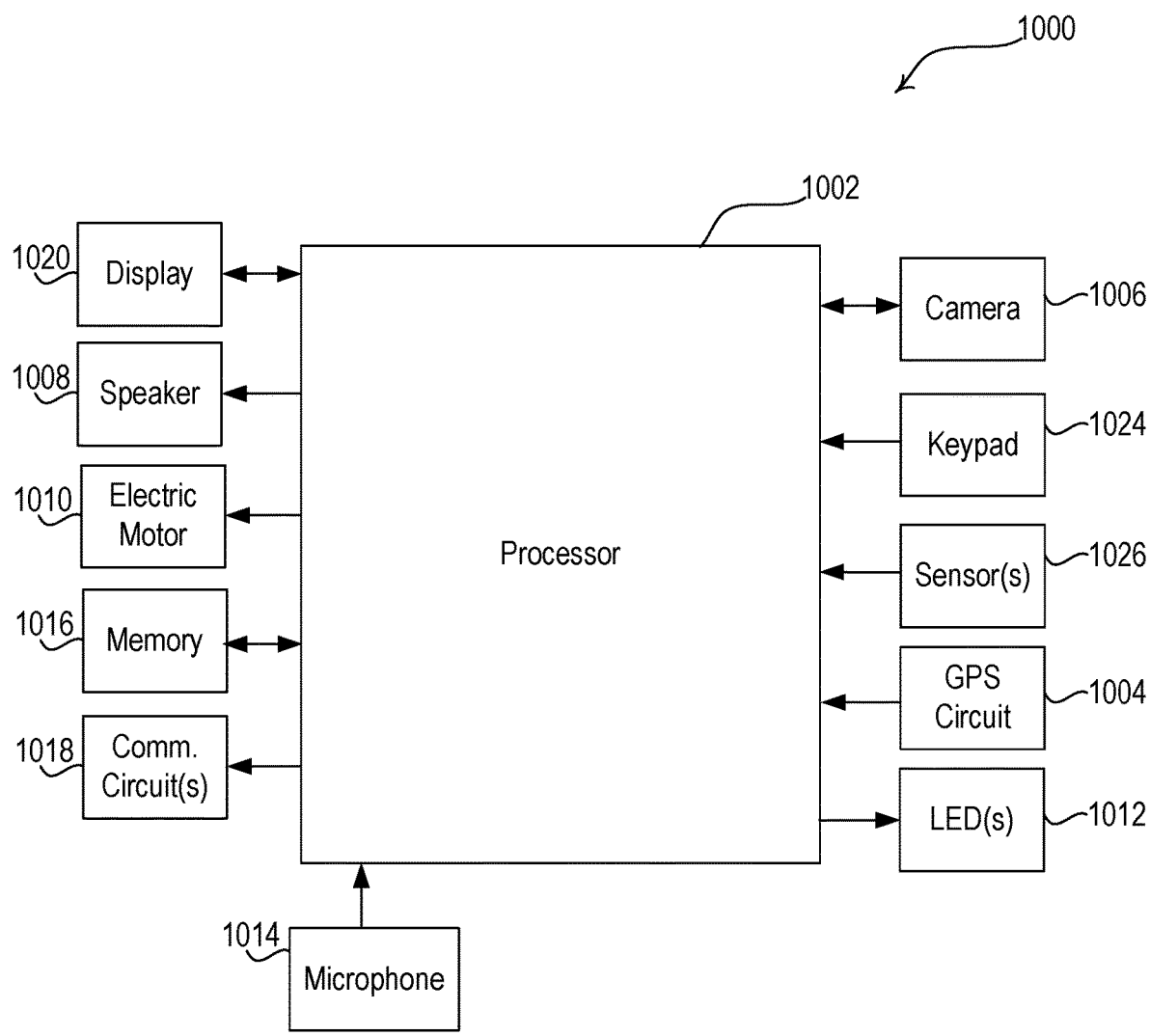
FIG. 10 is a block diagram of an example computing device.

FIG. 10 is a block diagram of an example computing device 1000. The computing device is a mobile computing device, such as a tablet, a cellular phone, a wearable device, a CGM controller device, or another computing device, for example. As shown in FIG. 10, the computing device 1000 includes a processor 1002 for controlling the functionality of the computing device 1000. The processor 1002 includes one or more circuits, such as general-purpose processors, special purpose processors, conventional processors, digital signal processors (DSPs), microprocessors, integrated circuits, a programmable logic device (PLD), application specific integrated circuits (ASICs), or the like. The processor 1002 performs signal coding, data processing, power control, image processing, input/output processing, or any other functionality that enables the computing device 1000 to perform as described herein.

The processor 1002 stores information in or retrieve information from the memory 1016. The memory 1016 includes a non-removable memory or a removable memory. The non-removable memory may include random-access memory (RAM), read-only memory (ROM), a hard disk, or any other type of non-removable memory storage. The removable memory may include a subscriber identity module (SIM) card, a memory stick, a memory card (e.g., a digital camera memory card), or any other type of removable memory. The processor 1002 accesses the memory 1016 for executable instructions or other information that is used by the computing device 1000.

The computing device 1000 includes a camera 1006 that is in communication with the processor 1002. The camera 1006 is a digital camera or other optical device capable of generating images or videos (e.g., image sequences) for being captured at the computing device 1000. The camera 1006 includes a lighting device capable of flashing to in response to signals from the processor 1002. The lighting device flashes to provide alerts via the camera 1006.

The computing device 1000 includes one or more communication circuits 1018. The processor 1002 is in electrical communication with the communication circuit 1018 for sending or receiving information. The communication circuit 1018 is capable of performing wired or wireless communications. For example, the communication circuit 1018 includes one or more radio frequency (RF) transceivers for transmitting and receiving RF signals (e.g., BLUETOOTH®, near field communication (NFC), WIFI®, WI-MAX®, cellular, or other suitable wireless transceivers) via an antenna, or other communications module capable of performing wireless communications. One or more communication circuits 1018 are capable of performing infrared (IR) communications.

The processor 1002 is in electrical communication with a keypad 1024 for providing input to the processor 1002. The keypad 1024 includes one or more keys for receiving input from a user. The keypad 1024 includes hard or soft keys for which the function of the keys may change as a user performs selections.

Other input into the processor 1002 is provided by one or more sensors 1026. The sensors 1026 includes a motion sensor, a proximity sensor, a heartrate monitoring sensor, an accelerometer, a gyroscope, or another sensor on the computing device. The motion sensor transmits infrared signals or use image processing to sense movement. The proximity sensor transmits infrared signals to detect when an object is within a predefined proximity. The heartrate monitoring sensor implements photoplethysmography to detect the amount of blood flow in the user. The heartrate monitoring sensor includes one or more LED or photodiodes to detect the amount of blood flow in the user. The heartrate monitoring sensor implements infrared technology to detect the amount of blood flow in the user. The heartrate monitoring sensor takes an electrocardiogram (ECG) and detects information about the user's heartrate from the ECG. The accelerometer measures the non-gravitational acceleration of the computing device 1000 in a given direction. The accelerometer responds to vibrations associated with movement in a given direction. The measurements from the accelerometer are used by the processor 1002 to determine the magnitude or direction of the relative movement of the computing device 1000, or the user's relative position (e.g., standing, sitting, or lying down). The gyroscope is used to determine the orientation of the computing device 1000.

The processor 1002 is in electrical communication with or generate images on a display 1020 for providing information to a user. The communication between the display 1020 and the processor 1002 is a two-way communication, as the display 1020 includes a touch screen module capable of receiving information from a user and providing such information to the processor 1002. For example, the display 1020 provides soft buttons for selection by a user that are recognized by the touch screen module and provided to the processor 1002 as input.

The processor 1002 is in electrical communication with or control a speaker 1008. The speaker 1008 provides an audible sound (e.g., tone, beep, or buzz) in response to a triggering event detected by the processor 1002.

The computing device 1000 includes an electric motor 1010 that is in electrical communication with or controlled by the processor 1002. The electric motor 1010 rotates and causes the computing device 1000 to vibrate (e.g., to indicate an alert) in response to a triggering event detected by the processor 1002. The electric motor 1010 provides an alert to supplement the audible alarm or replace the audible alarm provided by the speaker 1008.

The processor 1002 is in electrical communication with or receive information from a microphone 1014. For example, the processor 1002 receives audio signals via the microphone 1014.

The computing device 1000 includes a global positioning system (GPS) circuit 1004. The GPS circuit 1004 is capable of receiving GPS information. The processor 1002 is capable of determining the GPS coordinates (e.g., latitude and longitude) of the computing device 1000 based on the GPS information received via the GPS circuit.

The computing device 1000 includes a visual indicator, such as one or more one or more light-emitting diodes (LEDs) 1012. One or more LEDs 1012 are illuminated or flashed to provide an alert or communicate other information to the user (e.g., low battery or turning on of the device).

Figure 11:
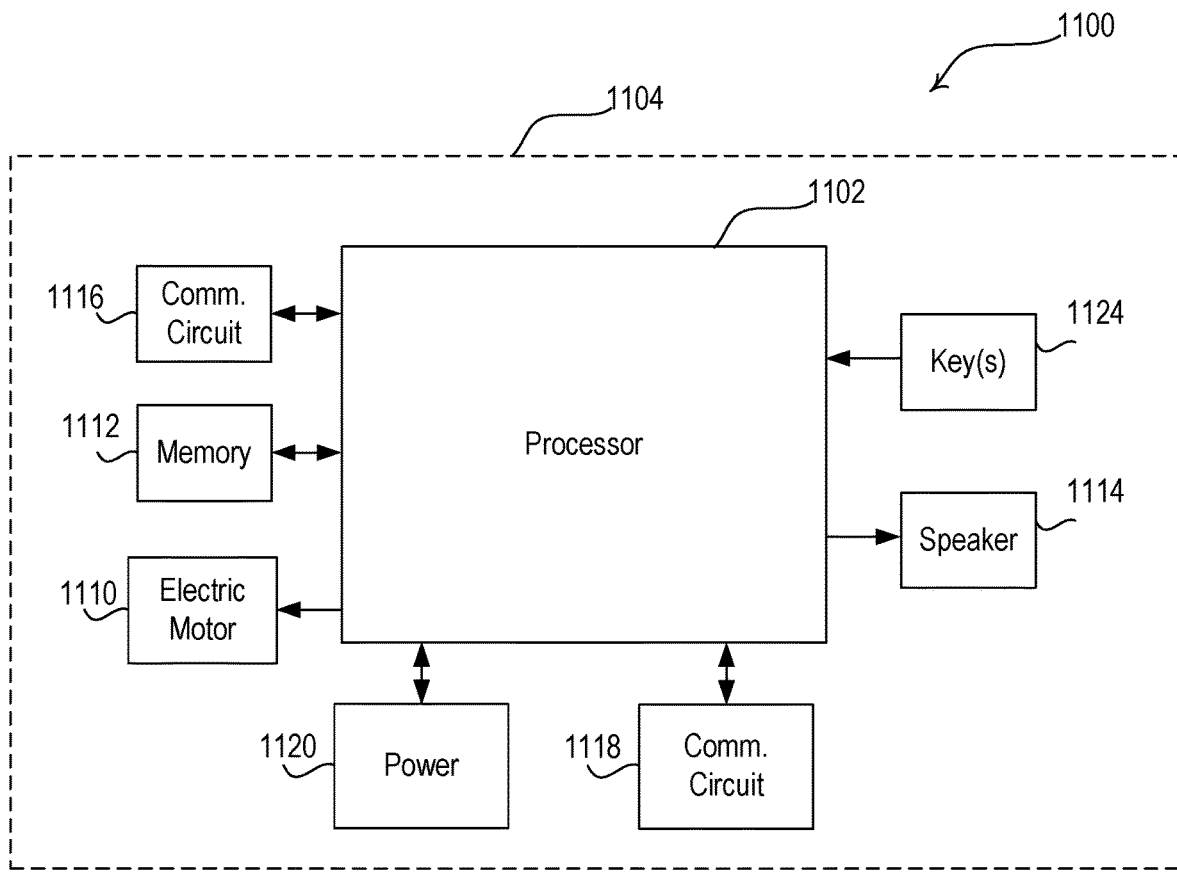
FIG. 11 is a block diagram of an example blood glucose monitoring device.
Figure 11:
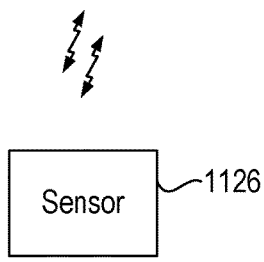

FIG. 11 is a block diagram of an example blood glucose monitoring device 1100. The blood glucose monitoring device 1100 is a CGM or FGM, for example. The blood glucose monitoring device 1100 includes a subcutaneous sensor 1126 that is used to sense and monitor the amount of glucose in interstitial fluid of the user. Data is transmitted from the sensor 1126 to a transmitting device 1104. When the blood glucose monitoring device 1100 is a CGM, the transmitting device 1104 is located directly over the sensor 1126 and wirelessly powers the data transfer from the sensor 1126 via power supply 1120. When the blood glucose monitoring device 1100 is an FGM, the transmitting device 1104 is a mobile device or other reader device that instantaneously receives the blood glucose information from the sensor 1126 when the device is within the RF range of the sensor 1126.

The transmitting device 1104 receives data communications from the sensor 1126 via a communication circuit 1118. The communication circuit 1118 is in electrical communication with a processor 1102. The processor 1102 includes one or more circuits, such as general-purpose processors, special purpose processors, conventional processors, digital signal processors (DSPs), microprocessors, integrated circuits, a programmable logic device (PLD), application specific integrated circuits (ASICs), or the like. The processor 1102 performs signal coding, data processing, power control, input/output processing, or any other functionality that enables the transmitting device 1104 to perform as described herein.

The transmitting device 1104 includes another communication circuit 1116 for communicating with other devices. The processor 1102 is in electrical communication with the communication circuit 1116 for sending or receiving information. The communication circuits 1116, 1118 are capable of performing wired or wireless communications. For example, the communication circuits 1116, 1118 includes one or more radio frequency (RF) transceivers for transmitting and receiving RF signals (e.g., BLUETOOTH®, near field communication (NFC), WIFI®, WI-MAX®, cellular, or other suitable RF signals) via an antenna, or other communications module capable of performing wireless communications. The communication circuits 1116, 1118 communicate using the same RF protocol or a different RF protocol.

The processor 1102 stores information in or retrieves information from the memory 1112. The memory 1112 includes a non-removable memory or a removable memory. The non-removable memory includes random-access memory (RAM), read-only memory (ROM), a hard disk, or any other type of non-removable memory storage. The removable memory includes a subscriber identity module (SIM) card, a memory stick, a memory card (e.g., a digital camera memory card), or any other type of removable memory. The processor 1102 accesses the memory 1112 for executable instructions or other information that is used by the transmitting device 1104. The processor 1102 is in electrical communication with a one or more input keys 1124 for providing input to the processor 1102.

The processor 1102 is in electrical communication with or controls a speaker 1114. The speaker 1114 provides an audible sound (e.g., tone, beep, or buzz) in response to a triggering event detected by the processor 1102.

The blood glucose monitoring device 1100 includes an electric motor 1110 that is in electrical communication with or controlled by the processor 1102. The electric motor 1110 rotates and causes the blood glucose monitoring device 1100 to vibrate (e.g., to indicate an alert) in response to a triggering event detected by the processor 1102. The electric motor 1110 provides an alert to supplement the audible alarm or replace the audible alarm provided by the speaker 1114.

Figure 12:
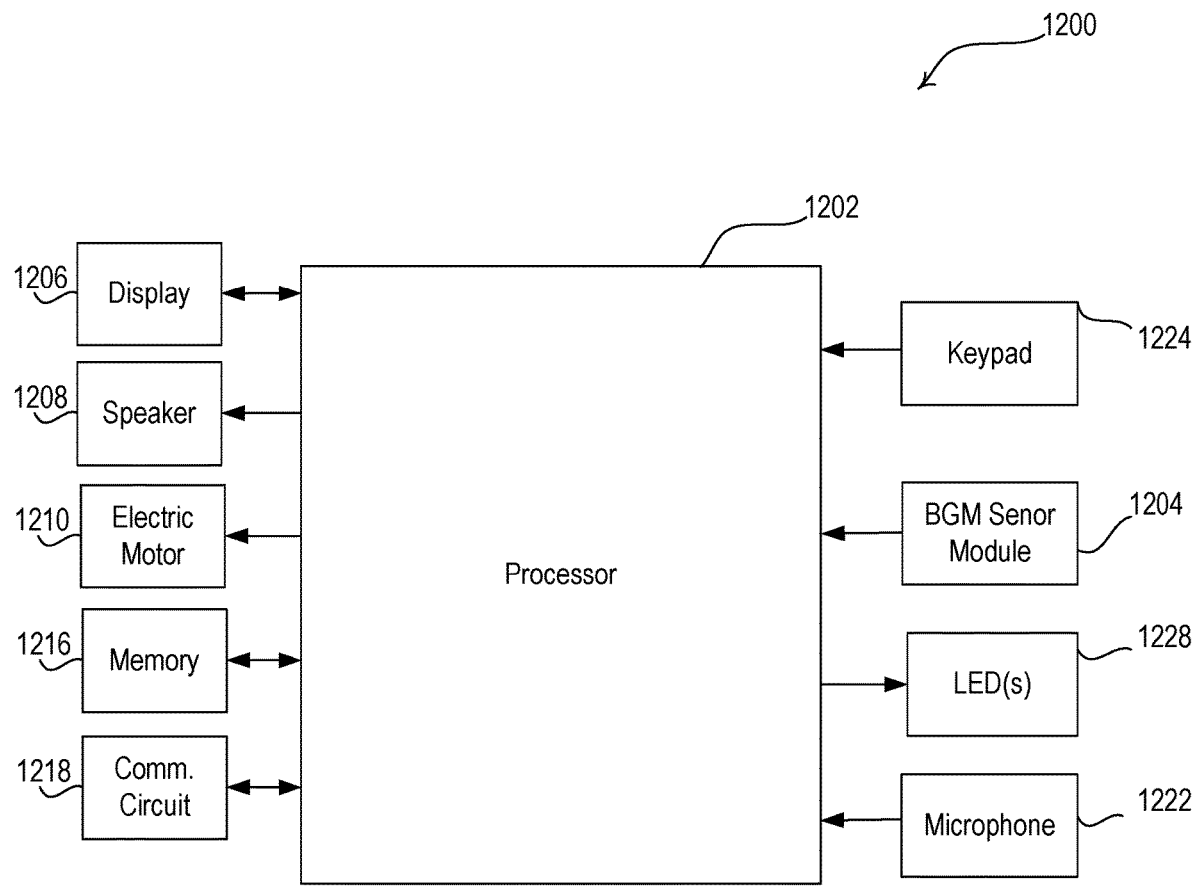
FIG. 12 is a block diagram of an example blood glucose measuring (BGM) device.

FIG. 12 is a block diagram of an example blood glucose measuring (BGM) device 1200. As shown in FIG. 12, the BGM device 1200 includes a processor 1202 for controlling the functionality of the BGM device 1200. In various embodiments, the processor 1202 includes one or more digital logic devices, such as general-purpose processors, special purpose processors, digital signal processors (DSPs), microprocessors, integrated circuits, programmable logic devices (PLDs), application specific integrated circuits (ASICs), and any other suitable digital logic device. The processor 1202 performs signal coding, data processing, power control, image processing, input/output processing, or any other functionality that enables the BGM device 1200 to perform as described herein.

The processor 1202 stores information in or retrieve information from the memory 1216. The memory 1216 includes a non-removable memory or a removable memory. The non-removable memory includes random-access memory (RAM), read-only memory (ROM), a hard disk, or any other type of non-removable memory storage. The removable memory includes a subscriber identity module (SIM) card, a memory stick, a memory card (e.g., a digital camera memory card), or any other type of removable memory. The processor 1202 accesses the memory 1216 for executable instructions or other information that is used by the BGM device 1200.

The BGM device 1200 includes one or more communication circuits 1218. The processor 1202 is in electrical communication with the communication circuit 1218 for sending or receiving information. The communication circuit 1218 is capable of performing wired or wireless communications. For example, the communication circuit 1218 includes one or more radio frequency (RF) transceivers for transmitting and receiving RF signals (e.g., BLUETOOTH®, near field communication (NFC), WIFI®, WI-MAX®, cellular, or other suitable RF signals) via an antenna, or other communications module capable of performing wireless communications. One or more communication circuits 1218 are capable of performing infrared (IR) communications.

The processor 1202 is in electrical communication with a keypad 1224 for providing input to the processor 1202. The keypad 1224 includes one or more keys for receiving input from a user. The keypad 1224 includes hard or soft keys for which the function of the keys may change as a user performs selections.

Other input into the processor 1202 is provided by the BGM sensor module 1204. The BGM sensor module 1204 includes a blood glucose measuring engine that analyzes blood samples provided by a patient on a blood glucose measurement strip and measures the amount of blood glucose in the samples.

The processor 1202 is in electrical communication with or generate images on a display 1206 for providing information to a user. The communication between the display 1206 and the processor 1202 is a two-way communication, as the display 1206 includes a touch screen module capable of receiving information from a user and providing such information to the processor 1202. For example, the display 1206 provides soft buttons for selection by a user that are recognized by the touch screen module and provided to the processor 1202 as input.

The processor 1202 is in electrical communication with or control a speaker 1208. The speaker 1208 provides an audible sound (e.g., tone, beep, or buzz) in response to a triggering event detected by the processor 1202.

The BGM device 1200 includes an electric motor 1210 that is in electrical communication with or controlled by the processor 1202. The electric motor 1210 rotates and causes the BGM device 1200 to vibrate (e.g., to indicate an alert) in response to a triggering event detected by the processor 1202. The electric motor 1210 provides an alert to supplement the audible alarm or replace the audible alarm provided by the speaker 1208.

The processor 1202 is in electrical communication with or receive information from a microphone 1222. For example, the processor 1202 receives audio signals via the microphone 1222.

The BGM device 1200 includes a visual indicator, such as one or more one or more light-emitting diodes (LEDs) 1228. One or more LEDs 1228 are illuminated or flashed to provide an alert or communicate other information to the user (e.g., low battery or turning on of the device).

Figure 13:
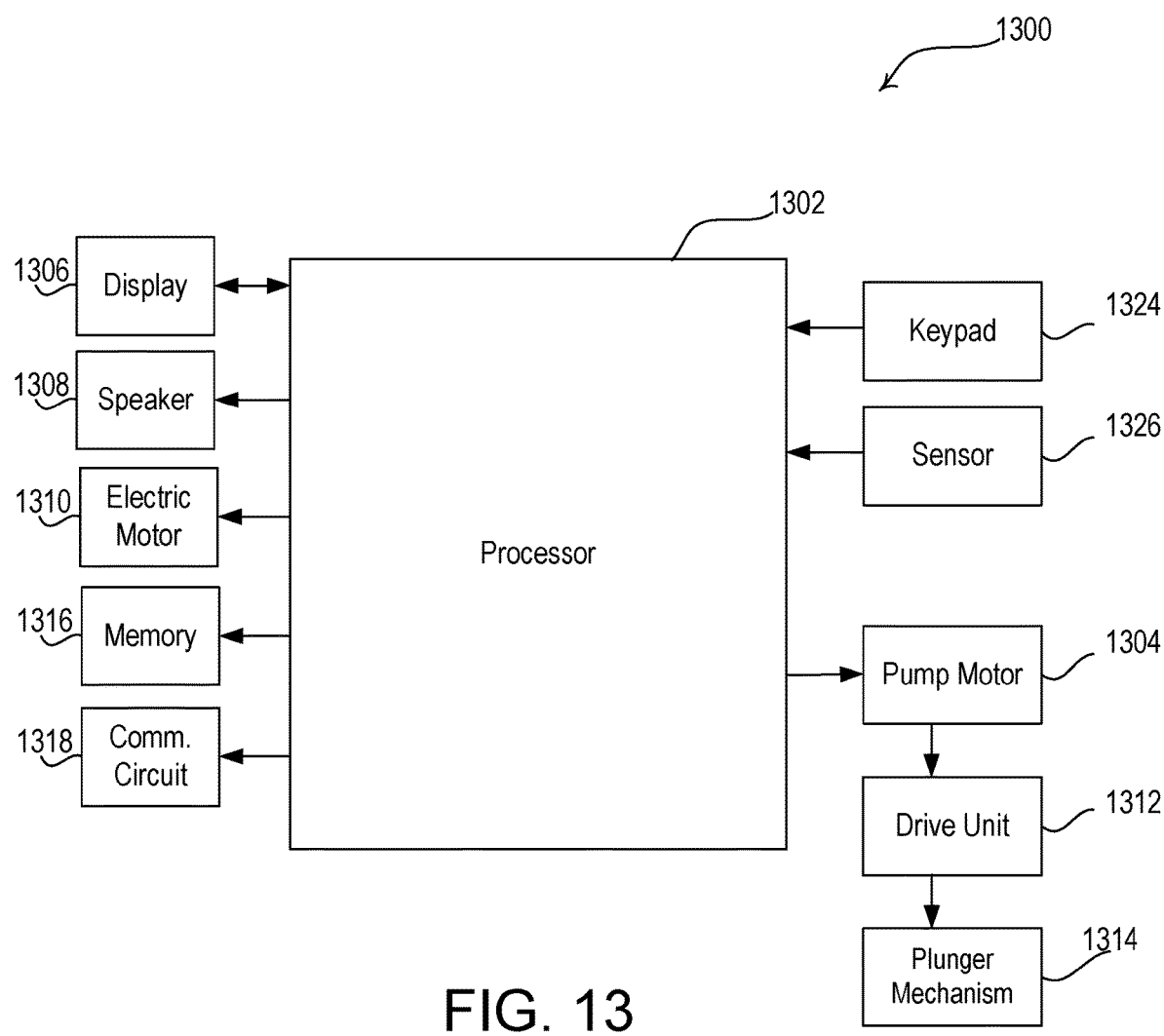
FIG. 13 is a block diagram illustrating an example of an insulin pump.

FIG. 13 is a block diagram illustrating an example of an insulin pump 1300. As shown in FIG. 13, the insulin pump 1300 includes a processor 1302. The processor 1302 includes one or more circuits, such as general-purpose processors, special purpose processors, conventional processors, digital signal processors (DSPs), microprocessors, integrated circuits, a programmable logic device (PLD), application specific integrated circuits (ASICs), or the like. The processor 1302 performs signal coding, data processing, power control, image processing, input/output processing, or any other functionality that enables the insulin pump 1300 to perform as described herein.

In the embodiment of FIG. 13, the processor 1302 is in electrical communication with or control a pump motor 1304 in the insulin pump 1300. The pump motor 1304 drives a drive unit 1312 that pushes a plunger mechanism 1314. The plunger mechanism 1314 ejects insulin from an insulin cartridge (not shown). The insulin cartridge includes a supply of insulin for delivery to a user.

The processor 1302 is in electrical communication with or generate images on a display 1306 for providing information to a user. The communication between the display 1306 and the processor 1302 is a two-way communication, as the display 1306 includes a touch screen module capable of receiving information from a user and providing such information to the processor 1302. For example, the display 1306 provides soft buttons for selection by a user that are recognized by the touch screen module and provided to the processor 1302 as input.

The processor 1302 is in electrical communication with or control a speaker 1308. The speaker 1308 provides an audible sound (e.g., tone, beep, or buzz) in response to a triggering event detected by the processor 1302.

The insulin pump 1300 includes an electric motor 1310 that is in electrical communication with or controlled by the processor 1302. The electric motor 1310 rotates and causes the insulin pump to vibrate (e.g., to indicate an alert) in response to a triggering event detected by the processor 1302. The electric motor 1310 provides an alert to supplement the audible alarm or replace the audible alarm provided by the speaker 1308.

The processor 1302 is in electrical communication with a memory 1316. The processor stores information in or retrieves information from the memory 1316. The memory 1316 includes a non-removable memory or a removable memory for storing computer-readable media. The non-removable memory includes random-access memory (RAM), read-only memory (ROM), a hard disk, or any other type of non-removable memory storage. The removable memory includes a subscriber identity module (SIM) card, a memory stick, a memory card (e.g., a digital camera memory card), or any other type of removable memory. The processor 1302 accesses the memory 1316 for executable instructions or other information that is used by the insulin pump 1300.

The insulin pump 1300 includes a communication circuit 1318. The processor 1302 is in electrical communication with the communication circuit 1318 for sending or receiving information. The communication circuit 1318 is capable of performing wired or wireless communications. For example, the wireless communications circuit 1318 includes a radio frequency (RF) transceiver for transmitting and receiving RF signals (e.g., BLUETOOTH®, near field communication (NFC), WIFI®, WI-MAX®, cellular, or other suitable RF signals) via an antenna, or other communications module capable of performing wireless communications. The communication circuit 1318 is capable of performing infrared (IR) communications.

The processor 1302 is in electrical communication with a keypad 1324 for providing input to the processor 1302. The keypad 1324 includes one or more keys for receiving input from a user. The keypad 1324 includes hard or soft keys for which the function of the keys may change as a user performs selections.

Other input into the processor 1302 is provided by sensors 1326. The sensors 1326 includes a pressure sensor that is sensitive to the pressure within a reservoir of insulin; a cartridge sensor that is sensitive to the presence of an insulin cartridge, or a motion sensor that detects the motion of a gear (not shown) in the drive unit 1312.

Although features, elements, and functions are described above in particular combinations, a feature, element, or function is used alone or in any combination with the other features, elements, or functions. Various presently unforeseen or unanticipated alternatives, modifications, variations, or improvements may be subsequently made that are also intended to be encompassed by the following claims.

The methods described herein are implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random-access memory (RAM), removable disks, and optical media such as CD-ROM disks, and digital versatile disks (DVDs).

What is claimed is:

1. A method comprising:
    detecting a triggering event for communicating a diabetes-related alert to a user;
    detecting a keyword from at least one of a calendar event title or a calendar event location;
    determining a first predefined alert profile based on the keyword from the at least one of the calendar event title or the calendar event location;
    determining a second predefined alert profile based on a keyword from a location of a mobile device associated with the user;
    generating the diabetes-related alert using a first alert type associated with the first predefined alert profile in response to the first alert type matching a second alert type associated with the second predefined alert profile; and
    generating the diabetes-related alert using one of the first alert type or the second alert type that has a higher priority in response to the first alert type failing to match the second alert type.

2. The method of claim 1, wherein the first alert type and the second alert type comprise at least one different vibration setting or volume setting.

3. The method of claim 1, further comprising:
    using a higher-priority alert profile in response to a failure of the mobile device to receive a user acknowledgement of the diabetes-related alert after a predefined period of time.

4. The method of claim 3, further comprising:
    receiving an indication of a user selection of a modality for at least one of the first predefined alert profile or the second predefined alert profile; and
    setting, based on the modality, a number of repetitions that the diabetes-related alert is communicated using at least one of the first alert type or the second alert type before progressing to a higher-priority modality.

5. The method of claim 1, wherein the first predefined alert profile is determined in response to the calendar event location comprising a street address that matches the street address of a location type.

6. The method of claim 1, the method further comprising:
    comparing the keyword in the calendar event title to keywords associated with a plurality of predefined alert profiles, wherein the first predefined alert profile is determined in response to the keyword in the calendar event title matching a keyword associated with the first predefined alert profile.

7. The method of claim 1, further comprising:
    comparing the keyword in the calendar event location to keywords associated with a plurality of predefined alert profiles, and wherein the first predefined alert profile is determined in response to the keyword in the calendar event location matching a keyword associated with the first predefined alert profile.

8. The method of claim 1, wherein the keyword in the calendar event location comprises a street address, the method further comprising:
    comparing the street address in the calendar event location to street addresses of a plurality of location types having predefined alert profiles, and wherein the first predefined alert profile is determined in response to the street address in the calendar event location matching the street address of the location type for the first predefined alert profile.

9. The method of claim 1, wherein the first predefined alert profile is determined by:
    identifying a street address of the calendar event location;
    detecting a metadata field in geographic data for the street address, wherein the metadata field indicates a location type; and
    determining the first predefined alert profile based on the metadata field indicating the location type such that the first predefined alert profile is set to be socially appropriate for the calendar event location.

10. The method of claim 1, further comprising:
    adding a third alert profile that has a third alert type that is different from the first alert type and the second alert type; and
    storing the third alert profile in association with a corresponding keyword for being detected from the at least one of the calendar event title or the calendar event location.

11. The method of claim 1, wherein the keyword is one of a plurality of keywords detected from the at least one of the calendar event title or the calendar event location, wherein each of the plurality of keywords is associated with a different predefined alert profile of a plurality of predefined alert profiles, and wherein the first predefined alert profile is a lowest priority alert profile of the plurality of predefined alert profiles.

12. The method of claim 11, further comprising:
    using a higher-priority alert profile of the plurality of predefined alert profiles associated with the plurality of keywords detected from the at least one of the calendar event title or the calendar event location in response to a failure of the mobile device to receive a user acknowledgement of the diabetes-related alert after a predefined period of time.

13. The method of claim 1, further comprising:
    receiving an indication of a user selection to use a single global alert type for communicating diabetes-related alerts to the user;
    detecting a second triggering event for communicating a second diabetes-related alert to the user; and
    using the single global alert type for communicating the second diabetes-related alert to the user.

14. The method of claim 1, wherein the first alert type comprises a non-auditory alert type, wherein the second alert type comprises an auditory alert type, and wherein the first alert type has a lower priority based on the non-auditory alert type.

15. The method of claim 1, further comprising:
using a hierarchy of alert profiles having alert types from a lowest-priority alert type to a highest-priority alert type in response to a failure of the mobile device to receive a user acknowledgement of the diabetes-related alert after predefined periods of time.

16. The method of claim 1, wherein the higher priority is based on a predefined discreetness level.

17. A device comprising:
a processor configured to:
detect a triggering event for communicating a diabetes-related alert to a user;
detect a keyword from at least one of a calendar event title or a calendar event location;
determine a first predefined alert profile based on the keyword from the at least one of the calendar event title or the calendar event location;
determine a second predefined alert profile based on a keyword from a location of a mobile device associated with the user;
generate the diabetes-related alert using a first alert type associated with the first predefined alert profile in response to the first alert type matching a second alert type associated with the second predefined alert profile; and
generate the diabetes-related alert using one of the first alert type or the second alert type that has a higher priority in response to the first alert type failing to match the second alert type.

18. The device of claim 17, wherein the first alert type and the second alert type comprise at least one different vibration setting or volume setting.

19. The device of claim 17, wherein the processor is further configured to use a higher-priority alert profile in response to a failure of the mobile device to receive a user acknowledgement of the diabetes-related alert after a predefined period of time.

20. The device of claim 19, wherein the processor is further configured to:
receive an indication of a user selection of a modality for at least one of the first predefined alert profile or the second predefined alert profile; and
set, based on the modality, a number of repetitions that the diabetes-related alert is communicated using at least one of the first alert type or the second alert type before progressing to a higher-priority modality.

21. The device of claim 17, wherein the processor is further configured to determine the first predefined alert profile in response to the calendar event location comprising a street address that matches the street address of a location type.

22. The device of claim 17, wherein the processor is further configured to:
compare the keyword in the calendar event title to keywords associated with a plurality of predefined alert profiles; and
determine the first predefined alert profile in response to the keyword in the calendar event title matching a keyword associated with the first predefined alert profile.

23. The device of claim 17, wherein the processor is further configured to:
compare the keyword in the calendar event location to keywords associated with a plurality of predefined alert profiles; and
determine the first predefined alert profile in response to the keyword in the calendar event location matching a keyword associated with the first predefined alert profile.

24. The device of claim 17, wherein the keyword in the calendar event location comprises a street address, and wherein the processor is further configured to:
compare the street address in the calendar event location to street addresses of a plurality of location types having predefined alert profiles, and
determine the first predefined alert profile in response to the street address in the calendar event location matching the street address of the location type for the first predefined alert profile.

25. The device of claim 17, wherein the processor being configured to determine the first predefined alert profile further comprises the processor being configured to:
identify a street address of the calendar event location;
detect a metadata field in geographic data for the street address, wherein the metadata field indicates a location type; and
determine the first predefined alert profile based on the metadata field indicating the location type such that the first predefined alert profile is set to be socially appropriate for the calendar event location.

26. The device of claim 17, wherein the processor is further configured to:
add a third alert profile that has a third alert type that is different from the first alert type and the second alert type; and
store the third alert profile in association with a corresponding keyword for being detected from the at least one of the calendar event title or the calendar event location.

27. The device of claim 17, wherein the keyword is one of a plurality of keywords detected from the at least one of the calendar event title or the calendar event location, wherein each of the plurality of keywords is associated with a different predefined alert profile of a plurality of predefined alert profiles, and wherein the first predefined alert profile is a lowest priority alert profile of the plurality of predefined alert profiles.

28. The device of claim 27, wherein the processor is further configured to:
use a higher-priority alert profile of the plurality of predefined alert profiles associated with the plurality of keywords detected from the at least one of the calendar event title or the calendar event location in response to a failure to receive a user acknowledgement of the diabetes-related alert after a predefined period of time.

29. The device of claim 17, wherein the processor is further configured to:
receive an indication of a user selection to use a single global alert type for communicating diabetes-related alerts to the user;
detect a second triggering event for communicating a second diabetes-related alert to the user; and
use the single global alert type for communicating the second diabetes-related alert to the user.

30. The device of claim 17, wherein the first alert type comprises a non-auditory alert type, wherein the second alert type comprises an auditory alert type, and wherein the first alert type has a lower priority based on the non-auditory alert type.

31. The device of claim 17, wherein the processor is further configured to:
 use a hierarchy of alert profiles having alert types from a lowest-priority alert type to a highest-priority alert type in response to a failure to receive a user acknowledgement of the diabetes-related alert after predefined periods of time.

32. The device of claim 17, wherein the higher priority is based on a predefined discreetness level.

\* \* \* \* \*